US011195615B1

(12) United States Patent
Harley et al.

(10) Patent No.: US 11,195,615 B1
(45) Date of Patent: Dec. 7, 2021

(54) METHOD AND SYSTEM FOR DISTRIBUTED MANAGEMENT OF IN VIVO EXPOSURE THERAPY

(71) Applicant: Zeriscope, Inc., Mount Pleasant, SC (US)

(72) Inventors: William G. Harley, Mount Pleasant, SC (US); Ronald Ettore Acierno, Houston, TX (US)

(73) Assignee: Zeriscope, Inc., Mount Pleasant, SC (US)

( * ) Notice: Subject to any disclaimer, the term of this patent is extended or adjusted under 35 U.S.C. 154(b) by 26 days.

(21) Appl. No.: 16/989,681

(22) Filed: Aug. 10, 2020

(51) Int. Cl.
*G16H 40/67* (2018.01)
*G16H 50/20* (2018.01)
(Continued)

(52) U.S. Cl.
CPC ........... *G16H 40/67* (2018.01); *A61B 5/0022* (2013.01); *A61B 5/0077* (2013.01); *A61B 5/02055* (2013.01); *A61B 5/1112* (2013.01); *A61B 5/1118* (2013.01); *A61B 5/369* (2021.01); *A61B 5/389* (2021.01); *A61B 5/7264* (2013.01); *A61B 5/7465* (2013.01); *G16H 10/60* (2018.01); *G16H 20/70* (2018.01); *G16H 50/20* (2018.01); *G16H 50/70* (2018.01); *G16H 80/00* (2018.01); *A61B 5/024* (2013.01); *A61B 5/0531* (2013.01);
(Continued)

(58) Field of Classification Search
CPC ........ G16H 40/67; G16H 10/60; G16H 50/70; G16H 50/20; G16H 20/70; G16H 80/00; G16H 40/63; A61B 5/639; A61B 5/389; A61B 5/0022; A61B 5/0077; A61B 5/02055; A61B 5/112; A61B 5/1118; A61B 5/7264; A61B 5/7465; A61B 5/024; A61B 5/0531; A61B 5/0816; A61B 2560/0252; A61B 2562/0219; A61B 2562/0271; A61B 2562/029; A61B 5/165; H04L 67/12
See application file for complete search history.

(56) References Cited

U.S. PATENT DOCUMENTS

2010/0010371 A1 1/2010 Zayfert et al.
2011/0245633 A1 10/2011 Goldberg et al.
(Continued)

FOREIGN PATENT DOCUMENTS

WO 2015138251 A1 9/2015

*Primary Examiner* — Patrick Fernandes
(74) *Attorney, Agent, or Firm* — Gregory Finch; Finch Paolino, LLC

(57) ABSTRACT

A multimodal data acquisition and communication system and method for distributed management of in vivo exposure (IVE) therapy. An exemplary system, method, and apparatus according to certain aspects of the present disclosure may include a patient interface comprising (a) one or more sensors configured to collect quantitative (e.g., physiological data) and qualitative data (e.g., video/audio data) from a patient user during an IVE therapy session, and (b) a mobile computing device, such as a smartphone, comprising a mobile software application configured to establish a data transfer interface with the one or more sensors and provide a graphical user interface to the patient user. The mobile computing device may be communicatively engaged with a cloud-based server over a wireless communications network to enable real-time collection, communication, storage and analysis of IVE data and bi-directional audio/video communication with at least one clinician client device.

20 Claims, 11 Drawing Sheets

(51) Int. Cl.
| | |
|---|---|
| *G16H 50/70* | (2018.01) |
| *G16H 10/60* | (2018.01) |
| *G16H 20/70* | (2018.01) |
| *A61B 5/00* | (2006.01) |
| *A61B 5/0205* | (2006.01) |
| *A61B 5/11* | (2006.01) |
| *G16H 80/00* | (2018.01) |
| *A61B 5/369* | (2021.01) |
| *A61B 5/389* | (2021.01) |
| *H04L 29/08* | (2006.01) |
| *A61B 5/024* | (2006.01) |
| *A61B 5/0531* | (2021.01) |
| *A61B 5/08* | (2006.01) |

(52) U.S. Cl.
CPC ..... *A61B 5/0816* (2013.01); *A61B 2560/0252* (2013.01); *A61B 2562/029* (2013.01); *A61B 2562/0219* (2013.01); *A61B 2562/0271* (2013.01); *H04L 67/12* (2013.01)

(56) References Cited

U.S. PATENT DOCUMENTS

| | | |
|---|---|---|
| 2015/0031964 A1 | 1/2015 | Bly et al. |
| 2020/0302825 A1 | 9/2020 | Sachs et al. |

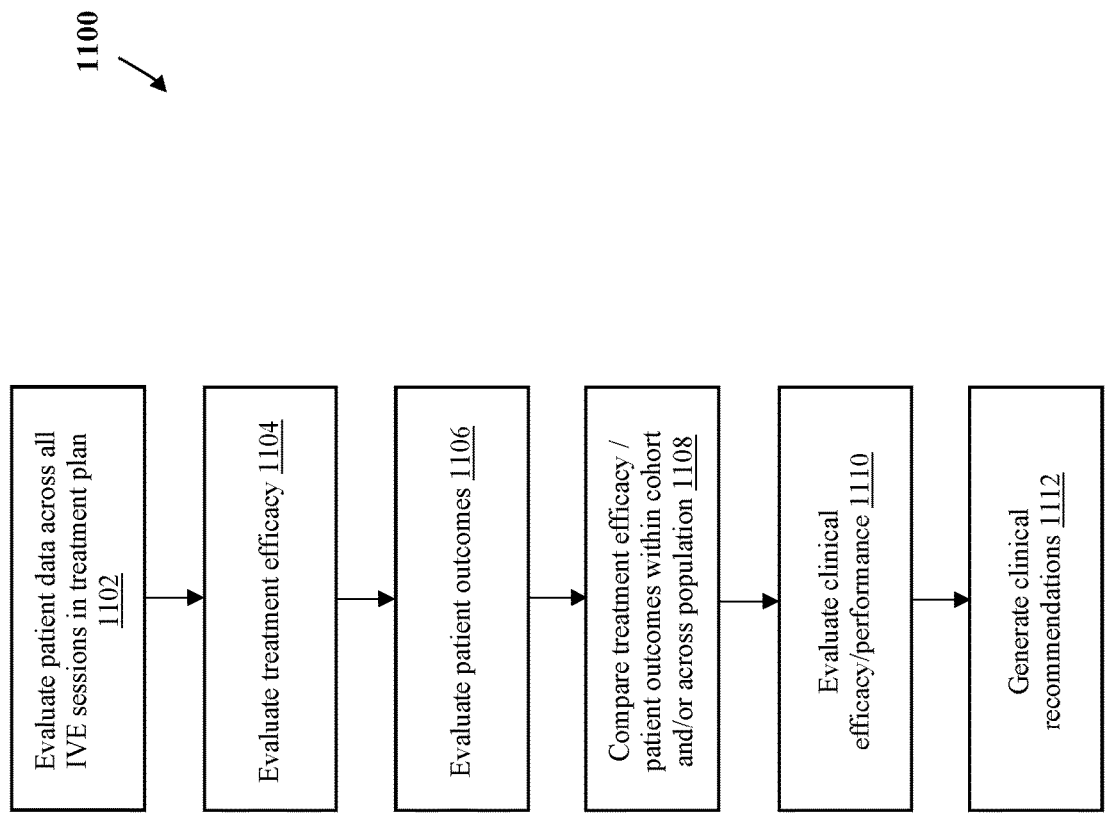

METHOD AND SYSTEM FOR DISTRIBUTED MANAGEMENT OF IN VIVO EXPOSURE THERAPY

STATEMENT REGARDING FEDERALLY SPONSORED RESEARCH OR DEVELOPMENT

This invention was made with government support under 1R43MH122045-01 awarded by National Institutes of Health. The government has certain rights in the invention.

FIELD

The present disclosure relates to the field of medical data acquisition and communication networks; more particularly, a multimodal data acquisition and processing system and method for distributed management of in vivo exposure therapy.

BACKGROUND

Posttraumatic Stress Disorder (PTSD) is a debilitating disorder in which a person has difficulty recovering after experiencing or witnessing a terrifying event. PTSD affects millions of American military veterans and civilians. PTSD may last months or years during which a patient may experience trigger events that bring back memories of the trauma accompanied by intense emotional and physical reactions. Symptoms may include nightmares or unwanted memories of the trauma, avoidance of situations that bring back memories of the trauma, heightened reactions, anxiety, or depressed mood. Treatment includes different types of trauma-focused psychotherapy as well as medications to manage symptoms. Prolonged exposure therapy is an intervention strategy commonly used in cognitive behavioral therapy to help individuals confront fears and treat anxiety disorders such as PTSD. Prolonged exposure is a specific type of cognitive behavioral therapy that teaches individuals to gradually approach trauma-related memories, feelings and situations. Most people want to avoid anything that reminds them of the trauma they experienced but doing so reinforces their fear. By facing what has been avoided, a person can decrease symptoms of PTSD by actively learning that the trauma-related memories and cues are not dangerous and do not need to be avoided.

Prolonged exposure is typically provided over a period of about three months with weekly individual sessions, resulting in eight to 15 sessions overall. The original intervention protocol was described as nine to twelve sessions, each 90 minutes in length. (Foa, E. B., & Rothbaum, B. O. *Treating the trauma of rape: Cognitive-behavioral therapy for PTSD.* 1998.) Sixty to 120-minute sessions are usually needed in order for the individual to engage in exposure and sufficiently process the experience. Therapists begin with an overview of treatment and understanding the patient's past experiences. Therapists continue with psychoeducation and then will generally teach a breathing technique to manage anxiety. Generally, after the assessment and initial session, exposure begins. As this is very anxiety-provoking for most patients, the therapist works to ensure that the therapy relationship is perceived to be a safe space for encountering such stimuli.

Prolonged exposure therapy is typically characterized by imaginal exposure and in vivo exposure (IVE). Imaginal exposure occurs in session with the patient describing the event in detail in the present tense with guidance from the therapist. Together, patient and therapist discuss and process the emotion raised by the imaginal exposure in session. The patient is recorded while describing the event so that she or he can listen to the recording between sessions and further process the emotions and practice the breathing techniques. IVE is exposure therapy in which the patient approaches safe but avoided stimuli in the "real world." The therapist and patient together identify a range of possible stimuli and situations connected to the traumatic fear, such as specific places or people. They agree on which stimuli to confront as part of in vivo exposure and devise a plan to do so between sessions. The patient is encouraged to challenge him or herself but to do so in a graduated fashion so as to experience some success in confronting feared stimuli and coping with the associated emotion. Typically, patients are given in vivo assignments to complete between therapy sessions, which leaves providers reliant on patient self-report and can increase risk for patient disengagement and dropout. While prolonged exposure therapy is evidence-based and effective, it is characterized by high dropout rates due to the high-stress nature of the treatment, and incomplete resolution of symptoms is seen in approximately one-third of patients.

Through applied effort, ingenuity, and innovation, Applicant has identified a number of deficiencies of the conventional approach to the clinical administration and management of IVE therapy. Applicant has developed a solution that is described in detail by the present disclosure provided below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present certain exemplified embodiments of the invention in a simplified form as a prelude to the more detailed description that follows.

Certain aspects of the present disclosure provide for a computer-implemented system for a computer-implemented system for distributed management of in vivo exposure therapy, comprising a patient interface comprising a mobile computing device having at least one input/output interface and at least one physiological sensor and at least one environmental sensor communicably engaged with the mobile computing device, wherein the mobile computing device is configured to present a graphical user interface of an in vivo exposure therapy application to a patient user; a clinician interface comprising a computing device having at least one input/output interface, wherein the clinician interface is configured to present a graphical user interface of the in vivo exposure therapy application to a clinician user; and a cloud-based server communicably engaged with the patient interface and the clinician interface via a communications network, the cloud-based server comprising at least one processor and at least one non-transitory computer-readable medium having instructions stored thereon that, when executed, cause the at least one processor to execute one or more operations of a server-instance of the in vivo exposure therapy application, the one or more operations comprising initiating a session of the in vivo exposure therapy application, the session comprising a patient-instance executing on the mobile computing device and a clinician-instance executing on the computing device; configuring one or more session parameters for the in vivo exposure therapy application, the one or more session parameters comprising parameters for exposure to at least one environmental stimulus for the patient user; receiving, at one or more timepoints, a plurality of patient data from the patient interface, the plurality of patient data comprising physiological sensor data, environmental sensor data and subjective unit of distress data for the patient user in response to the exposure to the at least one environmental stimulus; processing the plurality of patient data according to at least one machine learning framework to estimate one or more stimulus-response patterns between two or more of the environmental sensor data, the physiological sensor data and the subjective unit of distress data; communicating the plurality of patient data and the one or more estimated stimulus-response patterns to the computing device; modifying the one or more session parameters in response to one or more inputs from the clinician user; terminating the session of the in vivo exposure therapy application according to the one or more session parameters; and storing the plurality of patient data from the session in at least one database.

In accordance with certain embodiments, the one or more operations may further comprise establishing a real-time audio-video interface between the patient interface and the clinician interface. In accordance with certain embodiments, the at least one physiological sensor is selected from the group consisting of heart rate sensors, electrodermal activity sensors, respiration sensors, temperature sensors, actimetry sensors, accelerometers, EMG sensors, EEG sensors, and VOC sensors. In some embodiments, the patient interface further comprises at least one environmental sensor communicably engaged with the mobile computing device, wherein the at least one environmental sensor is selected from the group consisting of cameras, acoustic transducers, temperature sensors, GPS sensors, accelerometers, e-compass, gyroscopes, and humidity sensors. In accordance with certain aspects of the present disclosure, the plurality of patient data further comprises environmental sensor data from the at least one environmental sensor.

In accordance with certain aspects of the present disclosure, the computer-implemented system for distributed management of in vivo exposure therapy may be configured wherein the one or more operations further comprise evaluating one or more stimulus-response patterns between two or more of the environmental sensor data, the physiological sensor data and the subjective unit of distress data. The one or more operations may further comprise processing the plurality of patient data according to the at least one machine learning framework to classify at least one primary endpoint or dependent variable within the patient data, wherein the primary endpoint or dependent variable comprises at least one diagnostic variable or prognostic variable. The one or more operations further comprise processing a classified dataset comprising the plurality of patent data according to the at least one machine learning framework to generate at least one clinical recommendation output, the at least one clinical recommendation output comprising at least one recommended modification to the one or more session parameters. The one or more operations may further comprise modifying the one or more session parameters according to the estimated one or more stimulus-response patterns. The one or more operations may further comprise comparing the plurality of patient data from the session to a plurality of patient data from one or more prior sessions of the in vivo exposure therapy application stored in the at least one database to determine a measure of change in the plurality of patient data from the session. In certain embodiments, the one or more operations may further comprise modifying one or more subsequent session parameters according to the measure of change in the plurality of patient data from the session.

Further aspects of the present disclosure provide for a computer-implemented method for distributed management of in vivo exposure therapy, comprising establishing, with a cloud-based server via a communications network, a data transfer interface between a patient client device and a clinician client device; configuring, with the cloud-based server, a session of an in vivo exposure therapy application, the session comprising a patient instance comprising a graphical user interface of the in vivo exposure therapy application executing on the patient client device and a clinician instance comprising a graphical user interface of the in vivo exposure therapy application executing on the clinician client device; initiating, with the cloud-based server, the session of the in vivo exposure therapy application; providing, with the patient client device, one or more user prompts to a patient user according to one or more session parameters, the one or more session parameters comprising parameters for exposure to at least one environmental stimulus; collecting, with the patient client device, a plurality of patient data at one or more timepoints during the session, the plurality of patient data comprising physiological sensor data, environmental sensor data and subjective unit of distress data for the patient user in response to the exposure to the at least one environmental stimulus; communicating, with the patient client device via the communications network, the plurality of patient data to the cloud-based server; processing, with the cloud-based server, the plurality of patient data according to at least one machine learning framework to estimate one or more stimulus-response patterns between two or more of the environmental sensor data, the physiological sensor data and the subjective unit of distress data; communicating, with the cloud-based server via the communications network, the plurality of patient data and the one or more estimated stimulus-response patterns to the clinician device; modifying or maintaining, with the clinician client device, the one or more session parameters according to the plurality of patient data and the one or more estimated stimulus-response patterns; and terminating, with the cloud-based server, the session of the in vivo exposure therapy application according to the one or more session parameters, wherein the one or more session parameters comprise at least one duration parameter, location parameter and targeted stimulus-response parameter for the exposure to the at least one environmental stimulus.

In accordance with certain aspects of the present disclosure, the computer-implemented method for distributed management of in vivo exposure therapy may further comprise establishing, with the cloud-based server, a real-time audio-video interface between the patient client device and the clinician client device. In certain embodiments, the plurality of patient data may further comprise environmental sensor data from at least one environmental sensor selected from the group consisting of cameras, acoustic transducers, temperature sensors, GPS sensors, accelerometers, e-compass, gyroscopes, and humidity sensors. In accordance with certain aspects of the present disclosure, the method may further comprise evaluating, with the cloud-based server, one or more stimulus-response patterns between two or more of the environmental sensor data, the physiological sensor data and the subjective unit of distress data. The method may further comprise modifying, with the cloud-based server, the one or more session parameters according to the evaluated one or more stimulus-response patterns. The method may further comprise storing, with the cloud-based server, the plurality of patient data from the session in at least one database. The method may further comprise processing, with the cloud-based server, the plurality of patient data according to the at least one machine learning framework to classify at least one primary endpoint or dependent variable within the patient data, wherein the primary endpoint or dependent variable comprises at least one diagnostic variable or prognostic variable. The method may further comprise processing, with the cloud-based server, a classified dataset comprising the plurality of patent data according to the at least one machine learning framework to generate at least one clinical recommendation output, the at least one clinical recommendation output comprising at least one recommended modification to the one or more session parameters. The method may further comprise modifying, with the clinician client device, the one or more session parameters according to the at least one clinical recommendation output.

In accordance with certain aspects of the present disclosure, the computer-implemented method for distributed management of in vivo exposure therapy may further comprise comparing, with the cloud-based server, the plurality of patient data from the session to a plurality of patient data from one or more prior sessions of the in vivo exposure therapy application stored in the at least one database to determine a measure of change in the plurality of patient data from the session. In accordance with certain embodiments, the method may further comprise configuring, with the cloud-based server, one or more subsequent session parameters according to the measure of change in the plurality of patient data from the session. The method may further comprise configuring, with the clinician client device, one or more subsequent session parameters according to the one or more stimulus-response metrics for the plurality of patient data. The method may further comprise generating, with the cloud-based server, one or more recommended parameters for exposure to at least one environmental stimulus according to the one or more stimulus-response patterns for the plurality of patient data. The method may further comprise generating, with the cloud-based server, one or more recommended parameters for exposure to at least one environmental stimulus according to the one or more stimulus-response patterns for the plurality of patient data.

Still further aspects of the present disclosure provide for a non-transitory computer-readable medium encoded with instructions for commanding one or more processors to perform one or more operations of an in vivo exposure therapy application, the one or more operations comprising initiating a session of the in vivo exposure therapy application, the session comprising a patient-instance executing on a patient client device and a clinician-instance executing on a clinician client device; configuring one or more session parameters for the in vivo exposure therapy application, the one or more session parameters comprising parameters for exposure to at least one environmental stimulus for a patient user; receiving, at one or more timepoints, a plurality of patient data from the patient client device, the plurality of patient data comprising physiological sensor data, environmental sensor data and subjective unit of distress data for the patient user in response to the exposure to the at least one environmental stimulus; processing the plurality of patient data according to at least one machine learning framework to estimate one or more stimulus-response patterns between two or more of the environmental sensor data, the physiological sensor data and the subjective unit of distress data; communicating the plurality of patient data and the one or more estimated stimulus-response patterns to the clinician client device; modifying the one or more session parameters in response to one or more inputs from a clinician user; terminating the session of the in vivo exposure therapy application according to the one or more session parameters; and storing the plurality of patient data and session data in at least one database.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 11 is a process flow diagram of a method for distributed management of in vivo exposure therapy, in accordance with certain aspects of the present disclosure.

DETAILED DESCRIPTION

Figure 1:
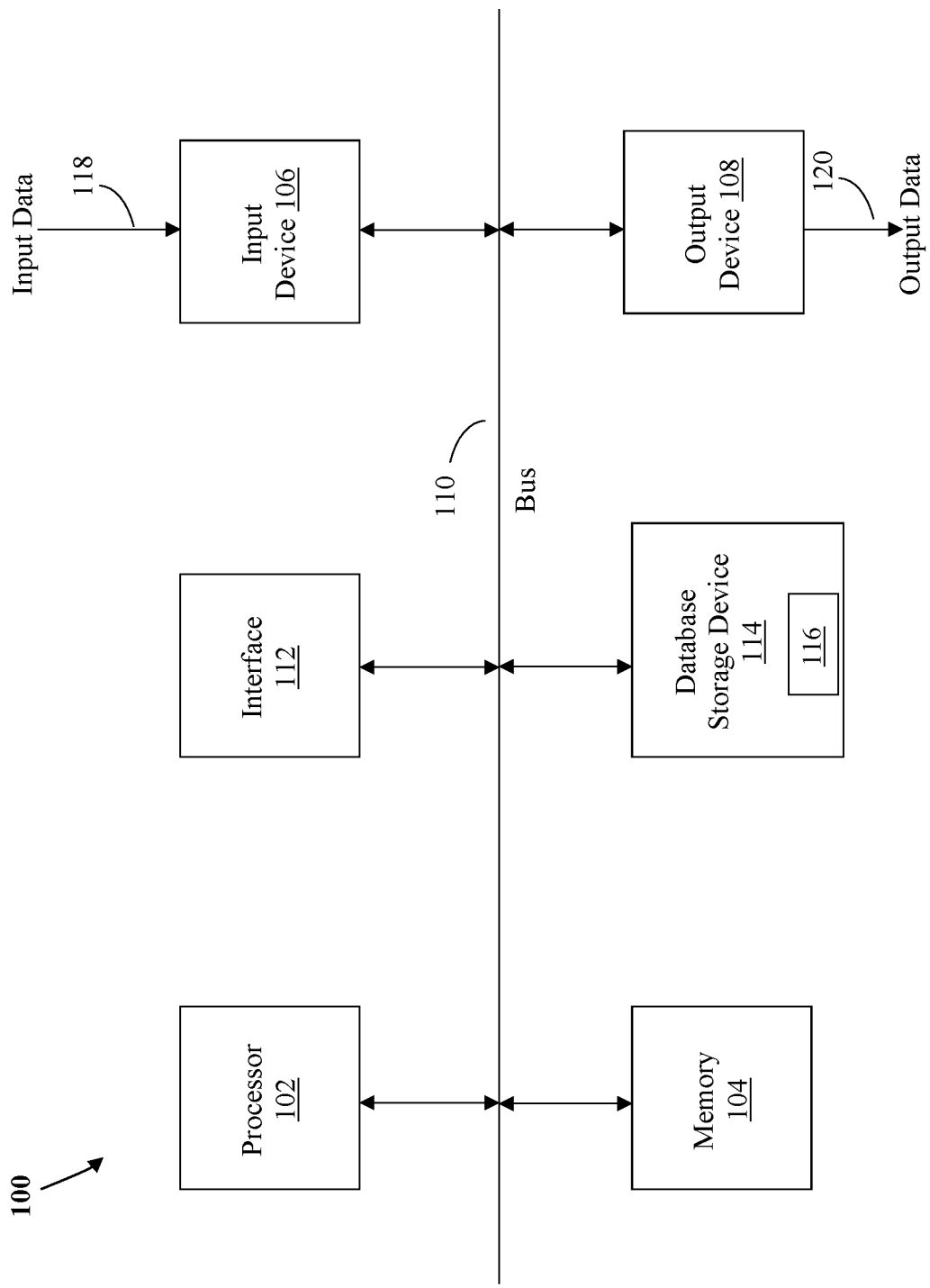
FIG. 1 is a block diagram of an exemplary computing device/system through which one or more aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, devices and systems configured to provide for multidimensional data acquisition and storage system to capture real-time biomarkers of engagement and patient reporting during in vivo exposure therapy.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "packet" refers to any formatted unit of data that may be sent and/or received by an electronic device.

As used herein, the term "payload" refers to any part of transmitted data that constitutes an intended message and/or identifying information.

As used herein, the term "patient" refers to any individual that is an end user of a patient client device and may further include individuals who are participating in prolonged exposure therapy comprising at least one in vivo exposure treatment.

As used herein, the term "clinician" refers to any individual that is an end user of a clinician client device and may further include individuals who are overseeing, managing or administering treatment of a patient.

As used herein, the term "interface" refers to any shared boundary across which two or more separate components of a computer system may exchange information. The exchange can be between software, computer hardware, peripheral devices, humans, and combinations thereof.

As used herein, the term "client" refers to any piece of computer hardware or software that accesses a service made available by a server.

As used herein, the term "native" refers to any software program that is installed on a mobile electronic device.

Certain benefits and advantages of the present disclosure include enhanced engagement and adherence to IVE exercises and improved clinical data collection and insights via real-time collection and communication of physiological biomarkers of affective engagement, including galvanic skin response (GSR), heart rate (HR) and subjective units of distress (SUDS). In accordance with certain aspects of the present disclosure, activity data may be collected, processed and analyzed in real-time to enable clinicians to modify exercises and avoid under- and over-engagement, thereby minimizing inefficiencies and maximizing therapeutic value of IVE session (IVEs). Passive data may be collected, processed and analyzed to characterize IVEs, identify predictors of change, and inform treatment decisions.

An exemplary system, method, and apparatus according to the principles herein may integrate physiological biomarker sensors with SUDS and audio/visual streaming to enable distributed administration and management of IVE. An exemplary system, method, and apparatus according to the principles herein may include a patient interface, clinician interface and a data storage and processing subsystem for analysis of IVE data. In accordance with certain aspects of the present disclosure, IVE data may be analyzed to identify biological and behavioral indicators with high predictive value of treatment response.

An exemplary system, method, and apparatus according to the principles herein includes a multidimensional data acquisition and storage system to capture real-time biomarkers of engagement (e.g., heart rate, skin conductance) and self-report (e.g., subjective units of distress or SUDS) during IVEs.

Certain benefits and advantages of the present disclosure include a biomarker-driven data collection and processing system to enhance IVE therapy for PTSD and link biomarkers of engagement (i.e. modifiable treatment targets) from IVEs to treatment outcomes. Embodiments of the present disclosure enable clinicians to virtually accompany patients during IVEs and modify the exercises in real-time based on objective biometrics of activation to ensure maximal efficiency and therapeutic benefit. Certain benefits and advantages of the present disclosure include the ability to collect, store and process multidimensional/multimodal data from IVEs in real-time and in real-world settings and analyze patient-specific physiological, behavioral and affective responses during IVEs.

Exemplary embodiments of the present disclosure include a patient-worn system to capture and transmit multidimensional/multimodal data during IVEs, as well as cloud-based data storage and an analysis system. Novel features also include an interactive clinician dashboard, two-way audio/video connection, and ability to record and store IVE data for future review and analysis and assign one or more data tags for the identification of potential "hot spots" during IVEs.

An exemplary system, method, and apparatus according to the principles herein includes one or more machine learning frameworks to analyze IVE data to determine, evaluate, identify and/or estimate one or more mechanisms of therapeutic change, identify modifiable treatment targets, personalize IVEs and improve patient outcomes.

An exemplary system, method, and apparatus according to the principles herein may include a patient interface comprising (a) a wearable device comprising one or more sensors configured to collect quantitative (e.g., physiological data) and qualitative data (e.g., video/audio data) from a patient user during an IVE session, and (b) a mobile computing device, such as a smartphone, comprising a mobile software application configured to establish a data transfer interface with the one or more sensors and provide a graphical user interface to the patient user. The mobile computing device may be communicatively engaged with a cloud-based server over a wireless communications network to enable real-time collection, communication, storage and analysis of IVE data and bi-directional audio/video communication with at least one clinician client device.

An exemplary system, method, and apparatus according to the principles herein may include a clinician interface comprising a mobile computing device or computer workstation communicatively engaged with a patient interface over a wireless communications network to enable bi-directional communication and data transfer. The clinician interface may comprise a graphical user interface configured to render/present IVE data collected and communicated from the patient device in real-time, including: digital video/audio data; physiological sensor data, such as heart rate data and galvanic skin response data; and user-generated data, such as SUDS ratings. The clinician interface may be communicatively coupled to an application server comprising at least one database to query, access and annotate IVE data stored in the at least one database.

An exemplary system, method, and apparatus according to the principles herein may include a HIPAA-compliant cloud-based/remote server comprising at least one database and being communicatively engaged with a patient interface and/or a clinician interface over a communications network to receive, store and/or process IVE data. The server may comprise a server-side software application configured to generate, store and assemble one or more individualized patient reports and enable analysis of IVE data across multiple IVEs.

Certain exemplary use cases of the system, method, and apparatus according to the principles herein may provide for distributed administration and management of IVE therapy in the treatment of anxiety disorders, such as PTSD, agoraphobia, social anxiety and other conditions such as substance use disorders. One or more patient interface may be communicably engaged with one or more server and/or clinician interface to enable bi-directional communication and enhanced data collection and analysis between a patient user and a clinician user before, during and after an IVE session.

Turning now descriptively to the drawings, in which similar reference characters denote similar elements throughout the several views, FIG. 1 depicts a computing system in which certain aspects of the present disclosure may be implemented.

Referring now to FIG. 1, a processor-implemented computing device in which one or more aspects of the present disclosure may be implemented is shown. According to an embodiment, a processing system 100 may generally comprise at least one processor 102, or a processing unit or plurality of processors, memory 104, at least one input device 106 and at least one output device 108, coupled together via a bus or a group of buses 110. In certain embodiments, input device 106 and output device 108 could be the same device. An interface 112 can also be provided for coupling the processing system 100 to one or more peripheral devices, for example interface 112 could be a PCI card or a PC card. At least one storage device 114 which houses at least one database 116 can also be provided. The memory 104 can be any form of memory device, for example, volatile or non-volatile memory, solid state storage devices, magnetic devices, etc. The processor 102 can comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or a wireless data adaptor, a data acquisition card, etc. Input data 118 can come from different sources, for example keyboard instructions in conjunction with data received via a network. Output device 108 produces or generates output data 120 and can comprise, for example, a display device or monitor in which case output data 120 is visual, a printer in which case output data 120 is printed, a port, such as for example a USB port, a peripheral component adaptor, a data transmitter or antenna such as a modem or wireless network adaptor, etc. Output data 120 can be distinct and/or derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 can be communicated to other devices via the network. The transfer of information and/or data over the network can be achieved using wired communications means or wireless communications means. A server can facilitate the transfer of data between the network and one or more databases. A server and one or more database(s) provide an example of a suitable information source.

Thus, the processing computing system environment 100 illustrated in FIG. 1 may operate in a networked environment using logical connections to one or more remote computers. In embodiments, the remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which embodiments of the invention may be implemented. That is, FIG. 1 is but an example of a suitable environment and is not intended to suggest any limitations as to the structure, scope of use, or functionality of embodiments of the present invention exemplified therein. A particular environment should not be interpreted as having any dependency or requirement relating to any one or a specific combination of components illustrated in an exemplified operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 100 of FIG. 1. As such, it will be understood that such acts and operations, which are at times referred to as being computer-executed, include the manipulation by the processor of the computer of electrical signals representing data in a structured form. This manipulation transforms data or maintains it at locations in the memory system of the computer, which reconfigures or otherwise alters the operation of the computer in a manner that is conventionally understood by those skilled in the art. The data structures in which data is maintained are physical locations of the memory that have particular properties defined by the format of the data. However, while certain embodiments may be described in the foregoing context, the scope of the disclosure is not meant to be limiting thereto, as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with embodiments of the invention include, but are not limited to, personal computers, handheld or laptop devices, personal digital assistants, multiprocessor systems, microprocessor-based systems, set top boxes, programmable consumer electronics, networks, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

With the exemplary computing system environment 100 of FIG. 1 being generally shown and discussed above, description will now turn towards illustrated embodiments of the present invention which generally relate to systems, devices, and methods for the distributed management of IVE therapy in the treatment of anxiety disorders, such as PTSD, agoraphobia, social anxiety and other conditions such as substance use disorders. It is to be understood and appreciated that certain aspects of the methods and system routines described herein comprise establishing a data transfer interface between a patient mobile electronic device and a clinician computing device; configuring a session of an in vivo exposure therapy application, the session comprising a patient instance comprising a graphical user interface executing on the patient mobile electronic device and a clinician instance comprising a graphical user interface executing on the clinician computing device; initiating the session of the in vivo exposure therapy application; providing one or more user prompts to a patient user according to one or more session parameters, the one or more session parameters comprising parameters for exposure to at least one environmental stimulus; collecting a plurality of patient data at one or more timepoints during the session, the plurality of patient user data comprising physiological sensor data and subjective unit of distress data for the patient user in response to the exposure to the at least one environmental stimulus; communicating the plurality of patient data to the clinician computing device; modifying or maintaining the one or more session parameters according to one or more stimulus-response metrics for the plurality of patient data; and terminating the session of the in vivo exposure therapy application according to the one or more session parameters.

Figure 2:
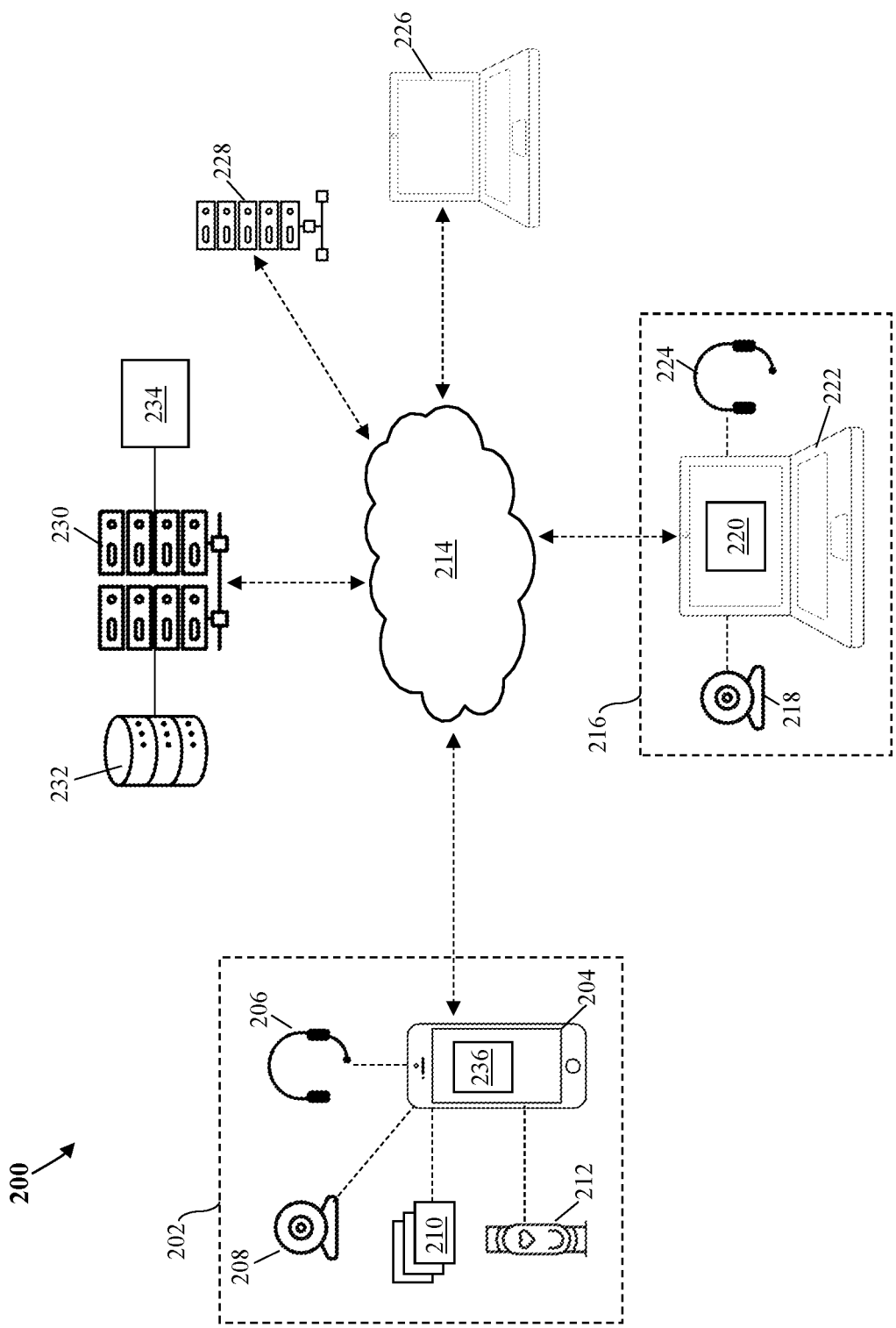
FIG. 2 is an architecture diagram of an in vivo exposure therapy management system, in accordance with certain aspects of the present disclosure.

Referring now to FIG. 2, an architecture diagram of an in vivo exposure therapy management system 200 is shown. In accordance with various aspects of the present disclosure, system 200 may be comprise various system elements and routines configured to collect, communicate, process, store, analyze and present data and derived variables associated with the clinical planning, administration and management of in vivo exposure therapy for the treatment of PTSD and other anxiety-related conditions (such as agoraphobia, social anxiety and certain related conditions, such as substance use disorders). System 200 may comprise a patient interface 202 comprised of one or more elements to enable the collection of multiple data types via multiple modalities, including data derived from a patient (e.g., physiological data via one or more wearable sensors and user-generated data via at least one input device) and data derived from an environment (e.g., audio and video data via one or more camera and/or microphone). In accordance with various embodiments, system 200 may comprise one or more routines for in situ data collection (e.g. data collected during an IVE therapy session) and ex situ data collection (e.g. data collected outside of an IVE therapy session).

In accordance with various aspects of the present disclosure, system 200 may be generally comprised of a patient interface 202, a clinician interface 216, and an application server 230. In certain embodiments, patient interface 202 may be associated with a patient (i.e. individual) who is the subject or participant in a prolonged exposure therapy regimen comprising one or more IVE therapy sessions. Clinician interface 216 may be associated with a clinician (i.e. therapist, doctor or other treatment provider) who is administering, managing and/or exercising clinical responsibility for the prolonged exposure therapy regimen comprising one or more IVE therapy sessions for the patient. In accordance with certain aspects of the present disclosure, patient interface 202 may comprise a patient client device 204, at least one physiological sensor 212, and one or more environmental sensors 210. Patient client device 204 may comprise a mobile electronic device such as a smart phone, tablet computer, or other hand-held computing interface. In certain embodiments, physiological sensor 212 may comprise one or more wearable sensor device, such as a smart watch or other wearable sensor device. In some embodiments, physiological sensor 212 may comprise a suite (i.e. two or more) of physiological sensors being either worn on the body of the patient or otherwise configured to collect physiological/biometric data associated with the patient. In certain embodiments, physiological sensor 212 may comprise one or more heart rate sensors, electrodermal activity sensors, respiration sensors, temperature sensors, actimetry sensors, accelerometers, EMG sensors, EEG sensors, and VOC sensors. Physiological/biometric data associated with the patient may comprise data indicative of, or associated with, heart rate, heart rate variability, electro-dermal activity, respiration, temperature, actigraphy, goniometry, tremor analyses, EEG, EMG, analysis of breath and saliva and the like. In certain embodiments, environmental sensors 210 may include one or more wearable sensor device, such as a heads-up display, a wearable camera, and/or a combination microphone/earpiece, and/or one or more environmental sensors 210 may be incorporated within patient client device 204. In some embodiments, environmental sensors 210 may comprise a suite (i.e. two or more) of environmental sensors being either being located on the person of the patient and/or otherwise configured to collect environment data in proximity to the patient. In certain embodiments, environmental sensors 210 may comprise one or more sensors including cameras, acoustic transducers, temperature sensors, GPS sensors, accelerometers, e-compass, gyroscopes, humidity sensors and the like. Environmental data may comprise audio-visual data, temperature, humidity, radiation, and data indicative of, or associated with, time and space of the patient (i.e. location, movement, and the like). In accordance with various aspects of the present disclosure, environmental sensors 210 and physiological sensors 212 are communicably engaged with patient client device 204 to provide a sensor input to a processing unit of patient client device 204. In accordance with certain embodiments, patient interface 202 may further comprise a camera 208 and audio input-output device 206. Camera 208 may comprise a handheld or body-worn camera communicably engaged with patient client device 204 and/or may comprise an internal camera of patient client device 204. Audio input-output device 206 may comprise a headset or headphones comprising a speaker and a microphone and/or may comprise an internal speaker and/or microphone of patient client device 204.

In accordance with certain embodiments, clinician interface 216 may comprise a clinician client device 222, a camera 218 and an audio input-output device 224. Clinician client device 222 may comprise a personal computer, laptop computer, smart phone, tablet computer or other personal computing device. Camera 218 may be an internal camera of clinician client device 222 and/or an external webcam or digital camera communicably engaged with clinician client device 222. Audio input-output device 224 may comprise a headset or headphones comprising at least one speaker and microphone and/or may comprise an internal microphone and speaker of clinician client device 222. In accordance with certain aspects of the present disclosure, patient interface 202 may be communicably engaged with clinician interface 216 over network 214. Network 214 may comprise an Internet connection, cellular communications network, LAN, WAN, and/or other network architecture operable to establish a data transfer interface between patient interface 202 and clinician interface 216. In certain embodiments, server 230 is a HIPAA-compliant server and network 214 comprises HIPAA-compliant communications network protocols. Server 230 may be configured as a cloud-based server.

In accordance with certain aspects of the present disclosure, application server 230 may be operably engaged with an application database 232 to host an IVE therapy management application 234. In accordance with certain embodiments, IVE therapy management application 234 may comprise processor executable instructions to command application server 230 to execute a variety of operations for IVE therapy management including, but not limited to, operations for establishing a data transfer interface between patient client device 204 and a clinician client device 222; configuring a patient-instance 236 of the IVE therapy management application for execution on patient client device 204; configuring a clinician-instance 220 of the IVE therapy management application for execution on clinician client device 222; facilitating data collection and transfer during an in vivo exposure session between patient interface 202, clinician interface 216 and application server 230; providing a graphical user interface within clinician instance 222 comprising one or more data visualizations; configuring one or more application parameters or settings to personalize or improve an in vivo exposure session for the patient user; determining one or more quantitative or qualitative treatment metrics for the patient user; generating one or more clinical insights for the clinician user; evaluating qualitative and/or quantitative measures of patient improvement or patient outcomes; evaluating treatment efficacy and/or clinician performance for the clinician user. In accordance with certain aspects of the present disclosure, application server 230 may be communicably engaged with one or more third-party servers 228 to receive or facilitate external data and/or services to enable one or more operations of application 234. Third-party servers 228 may comprise at least one electronic medical records server and external data may comprise electronic medical records data. System 200 may further comprise one or more stakeholder client device 226 communicably engaged with application server 230 via network 214 to query and access data stored in application database 232, such as patient outcome data, treatment efficacy data and/or clinician performance data. In certain embodiments, stakeholder client device 226 may be associated with a stakeholder user, such as an administrator of IVE therapy management application 234, a third-party payor (e.g. insurance provider), a caregiver or family member of a patient user, and/or a clinical administrator or researcher.

Figure 3:
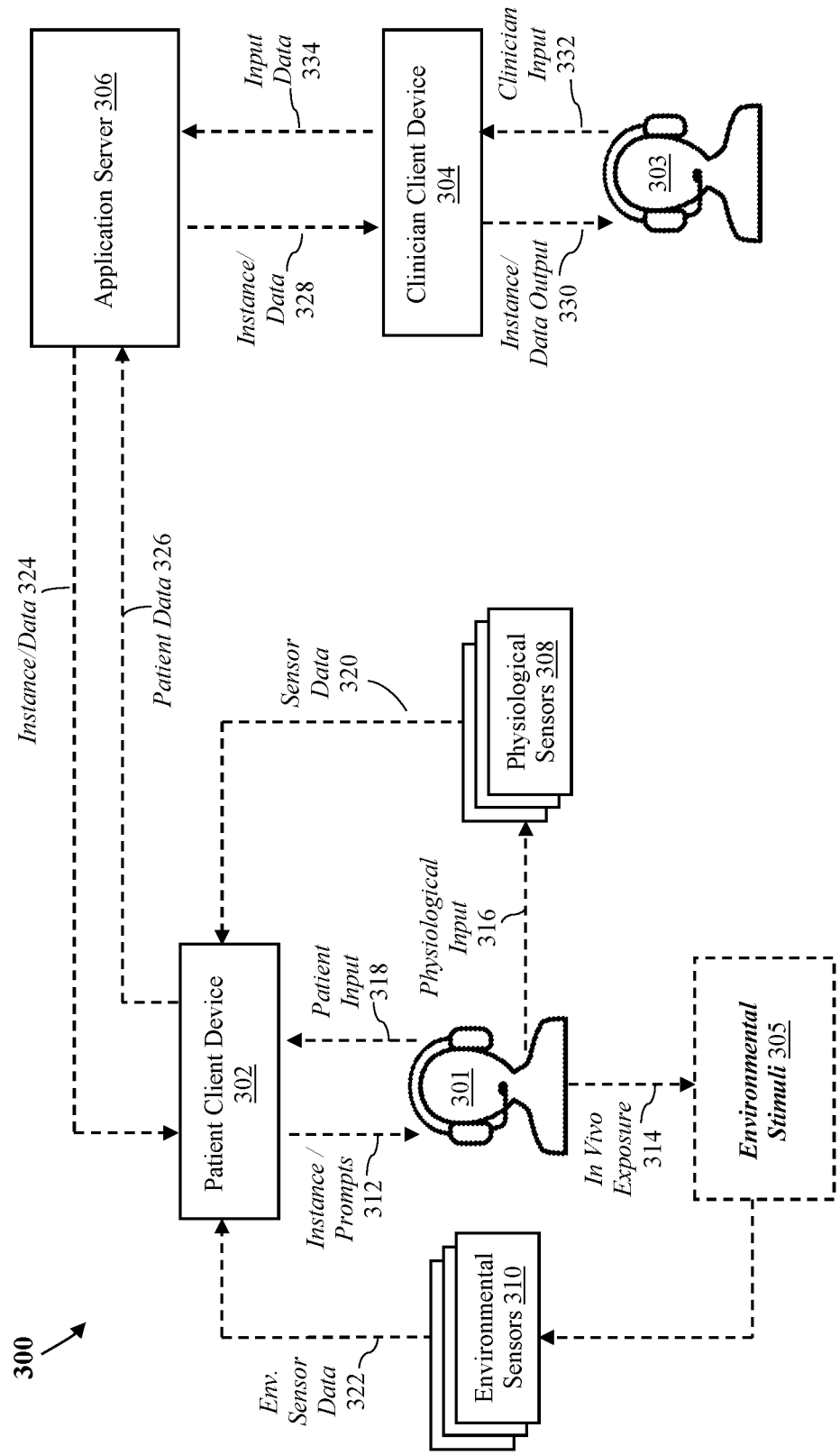
FIG. 3 is a functional diagram of an in vivo exposure therapy management system, in accordance with certain aspects of the present disclosure.

Referring now to FIG. 3, a functional diagram of an in vivo exposure therapy management system 300 is shown. In accordance with certain aspects of the present disclosure, system 300 may be embodied as system 200 of FIG. 2 and/or may comprise one or more system elements, routines or architectures of system 200 of FIG. 2. In accordance with certain aspects of the present disclosure, system 300 is configured to enable distributed management of an IVE therapy regimen between a clinician user 303 and a patient user 301. In accordance with certain exemplary use cases, system 300 may enable multidimensional data acquisition and storage to capture real-time biomarkers of engagement (e.g., heart rate, skin conductance) and self-report (e.g., subjective units of distress or SUDS) from patient user 301 during an IVE session, and enable clinician user 303 to modify prompts or tasks for patient user 301 during the IVE session based on biometrics of activation to ensure maximal efficiency and therapeutic benefit. An application server 306 may host and configure an IVE software application and may provision a clinician instance thereof to a clinician client device 304 and a patient instance thereof to a patient client device 302. The IVE software application may comprise a series of operations, workflows and protocols to enable the collection, communication, processing and storage of data generated across one or more pre-session, intra-session and post-session instances of the IVE software application.

Pre-Session Instance

In accordance with certain aspects of the present disclosure, system 300 may enable a series of operations, workflows and protocols within a pre-session instance of the IVE software application. In accordance with an embodiment, application server 306 may provision a pre-session instance of the IVE software application to clinician client device 304. Clinician client device 304 may render a graphical user interface of the pre-session instance of the IVE software application to clinician user 303. The graphical user interface of the pre-session instance of the IVE software application may comprise one or more interface elements comprising one or more pre-session workflows for completion by clinician user 303; for example, workflows for configuring a user profile for patient user 301, inputting baseline user or treatment data, and configuring one or more treatment plan elements. Clinician user 303 may provide one or more pre-session clinician inputs 332 via an input device of clinician client device 304 within the graphical user interface of the pre-session instance. Clinician client device 304 may communicate the clinician input data 334 to application server 306. Application server 306 may provision a pre-session instance of the IVE software application to patient client device 302. Patient client device 302 may render a graphical user interface of the pre-session instance of the IVE software application to patient user 301. The graphical user interface of the pre-session instance of the IVE software application may comprise one or more interface elements comprising one or more pre-session workflows for completion by patient user 301; for example, workflows for providing baseline or historical patient data (i.e. patient questionnaires or medical records) and collecting one or more pre-session or baseline physiological sensor inputs. Patient user 301 may provide one or more pre-session patient inputs 318 via an input device of patient client device 302 within the graphical user interface of the pre-session instance. Patient user 301 may also engage with physiological sensors 308 to capture one or more pre-session or baseline physiological input 316. In accordance with certain embodiments, the IVE software application may be configured to collect the one or more pre-session or baseline physiological input 316 at one or more time points across a set time period (e.g. one minute, one hour, one day, one week). Physiological sensors 308 may be communicably engaged with patient client device 302 to communicate sensor data 320 to patient client device 302. Patient client device 302 may communicate patient data 326, comprising patient inputs 318 and sensor data 320, to application server 306. Application server 306 may process patient data 326 and clinician input data 334 to configure one or more settings, parameters or configurations for patient user 301 and/or IVE treatment plan for patient user 301. Application server 306 may provide processed data 328 to clinician client device 304 to elicit one or more additional clinician inputs 332 from clinician 303 in order to configure the one or more settings, parameters or configurations for patient user 301 and/or IVE treatment plan for patient user 301.

IVE Session Instance

In accordance with certain aspects of the present disclosure, system 300 may enable a series of operations, workflows and protocols within an IVE session instance of the IVE software application. In accordance with an embodiment, application server 306 may provision an IVE session instance 324 to patient client device 302 and an IVE session instance 328 to clinician client device 304. IVE session instance 324 and IVE session instance 328 may be executed simultaneously on patient client device 302 and clinician client device 304 to enable real-time data transfer and bi-directional audio and/or video communication between patient client device 302 and clinician client device 304. Patient client device 302 may render a graphical user interface 312 of the IVE session instance to patient user 301. Graphical user interface 312 may comprise one or more interface elements to enable patient user 301 to begin an IVE therapy session and complete one or more user prompts or exercises. In accordance with certain aspects of the present disclosure, patient user 301 may initiate the IVE therapy session and engage in the one or more user prompts or exercises by engaging in in vivo exposure 314 to one or more environmental stimuli 305. The one or more user prompts or exercises may comprise completing certain tasks or exercises relating to environmental stimuli 305. Environmental stimuli 305 may include stimuli relating to various locations, situations, people and/or objects within the environment that trigger symptoms of an anxiety disorder for the patient. For example, if patient 301 suffers from PTSD triggered by shopping at grocery stores due to a traumatic experience that occurred in a grocery store, system 300 may configure one or more parameters for environment stimuli 305 accordingly. The pre-session data provided by patient user 301 and clinician user 303 is used to configure the IVE session parameters for in vivo exposure 314 and environmental stimuli 305. The one or more parameters for environmental stimuli 305 may comprise parameters such as location, timing, duration, and activity/actions (e.g. pushing a grocery cart through the produce section of a grocery store).

In accordance with certain embodiments, IVE session instance 328 may enable a real-time audio and/or video interface between patient client device 302 and clinician client device 304. The real-time interface may be configured to enable bi-directional communication between clinician user 303 and patient user 301 during in vivo exposure 314. During in vivo exposure 314, graphical user interface 312 may provide one or more input prompts to patient user 301. In certain embodiments, the one or more input prompts may be configured to elicit a reported SUDS score and/or other patient feedback prompts. Patient user 301 may provide one or more patient inputs 318 via an input device operably engaged with patient client device 302 in response to the one or more input prompts. Patient inputs 318 may further comprise one or more patient comments, subjective scores, and event tagging inputs. During in vivo exposure 314, physiological sensors may receive physiological input data 316 from patient user 301 and communicate sensor data 320 to patient client device 302. System 300 may further comprise one or more environmental sensors 310 communicably engaged with patient client device 302 and configured to collect real-time environmental sensor data 322 corresponding to environmental stimuli 305 during in vivo exposure 314. For example, environmental sensors 310 may comprise one or more cameras, acoustic transducers, temperature sensors, GPS sensors, accelerometers, e-compass, gyroscopes, humidity sensors and the like. Patient client device 302 may be configured to communicate patient data 326, comprising patient input data 318, sensor data 320 and environmental sensor data 322 to application server 306.

Application server 306 may be configured to execute one or more data processing steps and communicate, in real-time, the processed data to clinician client device 304 and render a graphical user interface 330 at clinician client device 304 comprising the processed data output. Clinician 303 may view the data in real-time and provide one or more clinician input 332 in response to the data. Clinician input 332 may comprise one or more data tagging input (e.g., hot spot tagging), clinician comments, and real-time session modifications or updates (e.g., modifying or creating a new task for in vivo exposure 314). Clinician client device 304 may communicate input data 334 comprising clinician inputs 332 to application server 306. Application server 306 may process input data 334 and provision real-time session modifications or updates, if relevant, to patient client device 302. Application server 306 may terminate the IVE session instance in response to patient data 326 satisfying one or more threshold values and/or upon expiration of a duration parameter. For example, the IVE session may terminate in response to a patient-reported SUDS input being reduced by a specified percentage and/or the patient's heartrate dropping within a designated range during in vivo exposure 314 and/or the environmental sensors data 322 being indicative of the patient 301 engaging in in vivo exposure 314 for a specified amount of time (e.g. 30 minutes). All data generated during the IVE session instance may be stored by application server 306 in an application database.

Post-Session Instance

In accordance with certain aspects of the present disclosure, system 300 may enable a series of operations, workflows and protocols within a pre-session instance of the IVE software application. In accordance with an embodiment, application server 306 may provision a post-session instance of the IVE software application to clinician client device 304. Clinician client device 304 may render a graphical user interface of the post-session instance of the IVE software application to clinician user 303. The graphical user interface of the post-session instance of the IVE software application may comprise one or more interface elements comprising one or more post-session workflows for completion by clinician user 303; for example, workflows for reviewing/analyzing session data, reviewing one or more clinical recommendations and/or biomarker data, and/or updating or modifying the one or more elements or parameters for the IVE treatment plan. Clinician user 303 may provide one or more post-session clinician inputs 332 via an input device of clinician client device 304 within the graphical user interface of the post-session instance. Clinician client device 304 may communicate the clinician input data 334 to application server 306. Application server 306 may provision a post-session instance of the IVE software application to patient client device 302. Patient client device 302 may render a graphical user interface of the post-session instance of the IVE software application to patient user 301. The graphical user interface of the post-session instance of the IVE software application may comprise one or more interface elements comprising one or more post-session workflows for completion by patient user 301; for example, workflows for feedback, scoring, self-assessments and/or comments from patient user 301 and collecting one or more post-session physiological sensor inputs. Patient user 301 may provide one or more post-session patient inputs 318 via an input device of patient client device 302 within the graphical user interface of the post-session instance. Patient user 301 may also engage with physiological sensors 308 to capture one or more post-session physiological input 316. In accordance with certain embodiments, the IVE software application may be configured to collect the one or more post-session physiological input 316 at one or more time points across a set post-session time period (e.g. post-session one minute, one hour, one day, one week). Physiological sensors 308 may be communicably engaged with patient client device 302 to communicate sensor data 320 to patient client device 302. Patient client device 302 may communicate patient data 326, comprising patient inputs 318 and sensor data 320, to application server 306. Application server 306 may process patient data 326 and clinician input data 334 to update, modify and/or configure one or more settings, parameters or configurations for patient user 301 and/or IVE treatment plan for patient user 301. Application server 306 may provide processed data 328 to clinician client device 304 to elicit one or more additional clinician inputs 332 from clinician 303 in order to configure the one or more settings, parameters or configurations for patient user 301 and/or IVE treatment plan for patient user 301.

Figure 4:
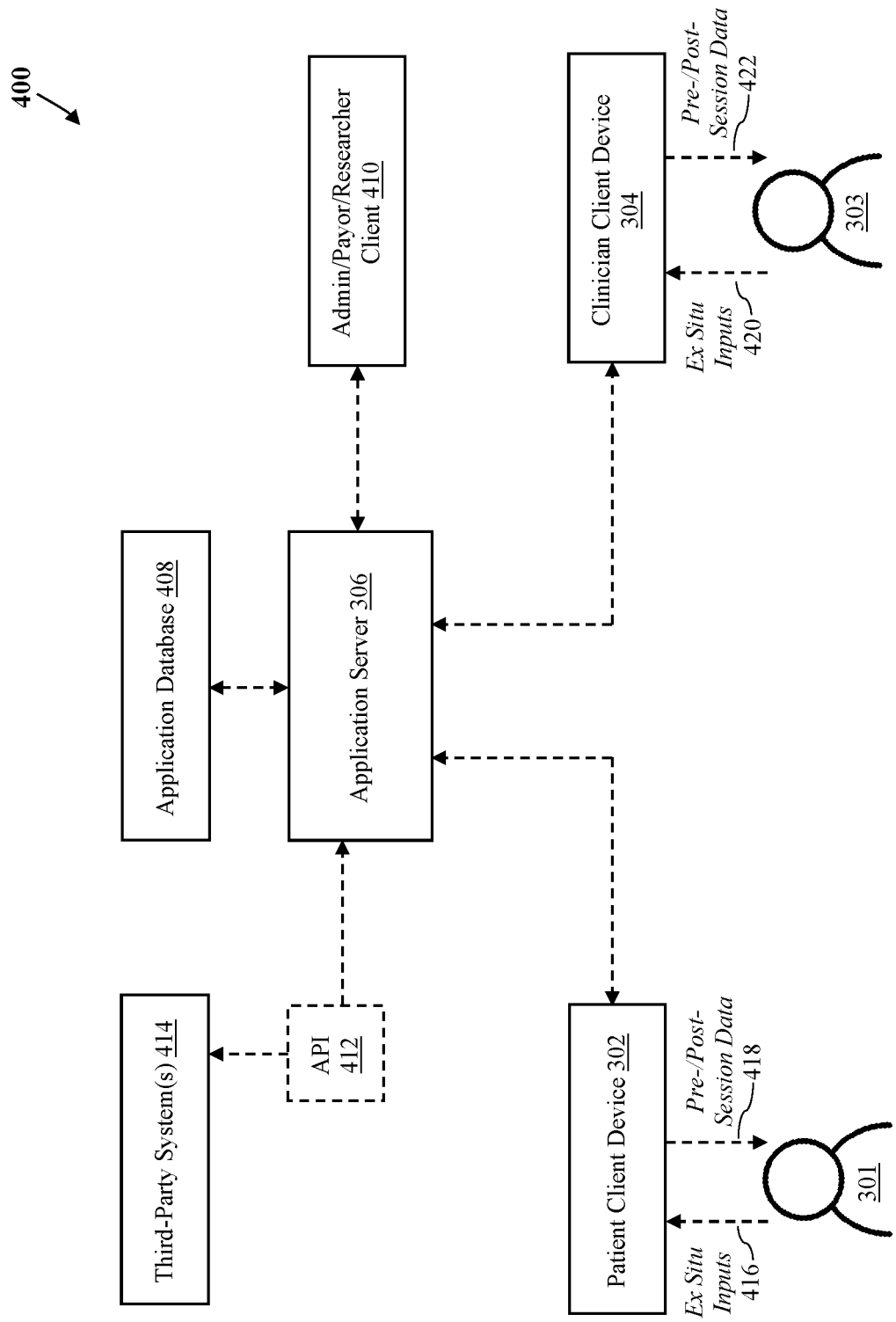
FIG. 4 is a functional diagram of an in vivo exposure therapy management system, in accordance with certain aspects of the present disclosure.

Referring now to FIG. 4, a functional diagram of an in vivo exposure therapy management system 400 is shown. In accordance with certain aspects of the present disclosure, one or more aspects of system 400 may be embodied within one or more aspects of system 200 of FIG. 2 and/or one or more aspects of system 300 of FIG. 3. In accordance with an embodiment, system 400 may be configured to process and analyze data across one or more sessions of an IVE therapy management application to analyze one or more variables; map data across session and/or between subjects across canonical groups of subjects; apply one or more machine learning framework(s) to analyze the data, generate one or more biomarkers being correlated to one or more patient outcomes; execute one or more automated actions to update, modify or improve treatment; and generate one or more clinical recommendations for a clinician user. In accordance with certain aspects of the present disclosure, application server 306 may be configured to provide one or more pre- or post-session data 418, 422 to patient user 301 via patient client device 302 and clinician client device 304. Clinician client device 304 may receive one or more ex situ inputs 420 from clinician user 303 and patient client device 302 may receive one or more ex situ inputs 416 from patient user 301. Application server 306 may execute one or more operations (as further described in FIGS. 5-7 below) to process the data according to one or more analytical frameworks and machine learning models. Application server 306 may be communicably engaged with one or more third-party systems 414 via application programming interface 412 to obtain external data comprising one or more longitudinal medical, behavioral, and contextual datasets. Application server 306 may be communicably engaged with at least one administrator, payor or researcher client 410 to query data within application database 408 and receive one or more processed data outputs from application server 306. Application server 306 may execute one or more routines to execute the data processing operations described above, as embodied by routines 500-700 described in FIGS. 5-7, below.

Figure 5:
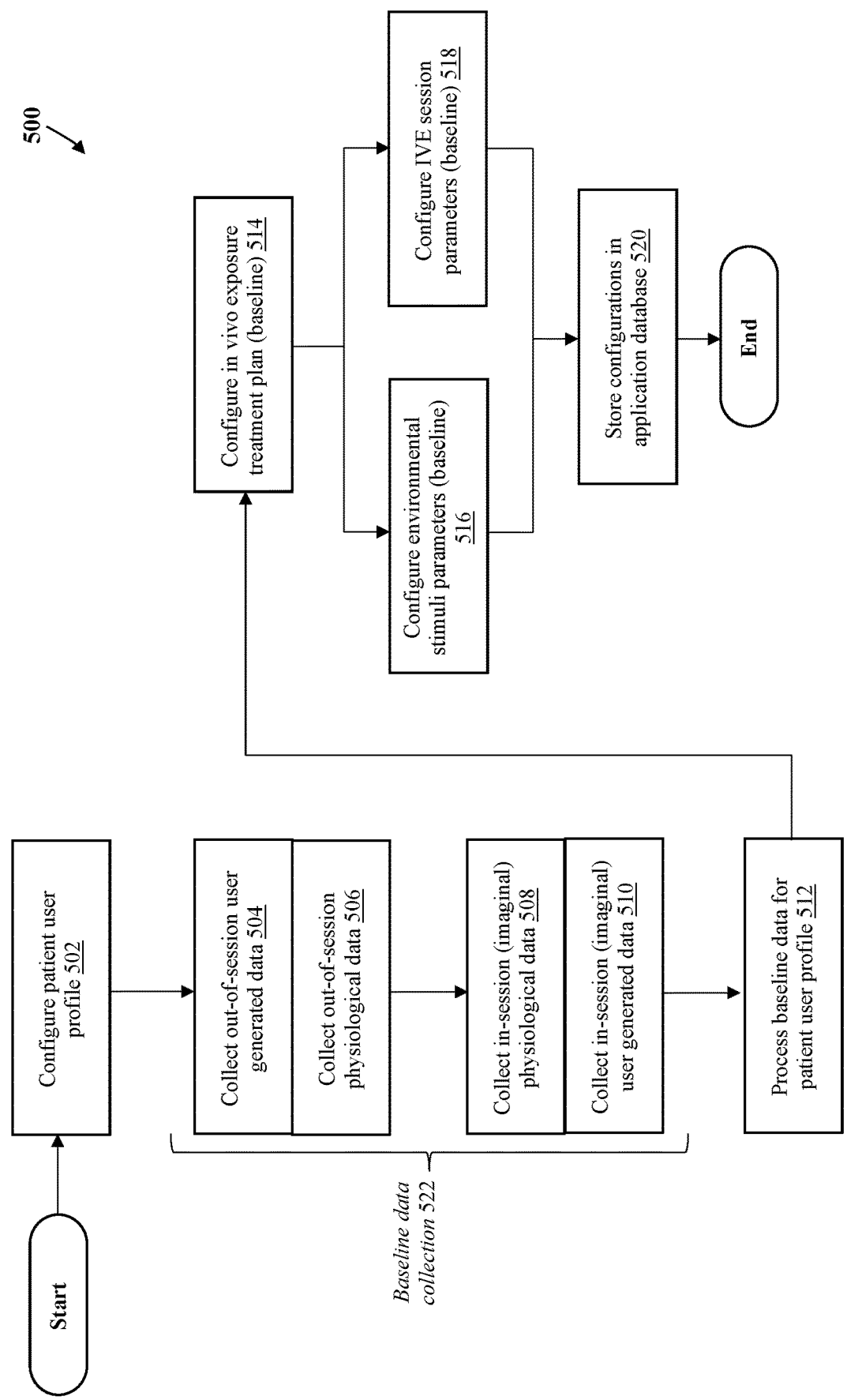
FIG. 5 is a process flow diagram of a routine of a method and system for distributed management of in vivo exposure therapy, in accordance with certain aspects of the present disclosure.

Referring now to FIG. 5, a process flow diagram of a routine 500 of a method and system for distributed management of in vivo exposure therapy is shown. In accordance with certain aspects of the present disclosure, routine 500 may be incorporated within one or more aspects of system 200 of FIG. 2, system 300 of FIG. 3 and/or system 400 of FIG. 4. Routine 500 may be incorporated within one or more process steps of data flow schema 800 of FIG. 8. Routine 500 may be embodied within one or more processor-executable instructions of an IVE therapy management application configured to command one or more operations of a patient client device, a clinician client device and/or an application server, as shown and described in FIGS. 2-4. In accordance with certain aspects of the present disclosure, routine 500 may comprise one or more of process flow steps 502-520. In certain embodiments, one or more of process flow steps 502-520 may comprise one or more sub-steps and/or may be executed via at least one processor of the patient client device, the clinician client device and/or the application server within a networked computing environment. Routine 500 may comprise one or more operations for establishing a patient user profile, collecting baseline patient data and configuring one or more IVE session parameters within the IVE therapy plan.

Still referring to FIG. 5, routine 500 may comprise one or more operations for configuring a patient user profile within an IVE therapy management application (Step 502). In certain embodiments, Step 502 may comprise presenting a graphical user interface to a clinician client device comprising at least one workflow for configuring a patient user profile. The clinician client device may communicate data for configuring the patient user profile to the application server, and the application server may execute one or more operations to establish the patient user profile in the application database. Routine 500 may comprise one or more baseline data collection steps 522 for collecting baseline data associated with the patient user profile. In accordance with certain embodiments, baseline data collection 522 may comprise one or more steps for collecting out-of-session user-generated data (Step 504) and collecting out-of-session physiological data (Step 506). Step 504 may comprise operations for launching an instance of the IVE therapy management application on the patient client device and presenting a graphical user interface configured to present one or more data collection workflows and/or form elements and receive one or more user-generated inputs according to the workflows and/or form elements. Step 506 may comprise one or more operations for establishing a data transfer interface between one or more physiological sensors and receiving a sensor input from the physiological sensors. In accordance with certain aspects of the present disclosure, Step 506 comprises operations for collecting out-of-session physiological data to determine one or more baseline physiological characteristics of the patient user. In accordance with certain embodiments, Step 506 may comprise one or more operations for collecting out-of-session physiological data over the course of specified time period(s) (e.g., one hour, three hours, six hours, 12 hours, 24 hours). In accordance with certain embodiments, baseline data collection 522 may comprise one or more steps for collecting in-session physiological data (Step 508) and collecting in-session user-generated data (Step 510). In accordance with certain aspects of the present disclosure, in-session physiological data and in-session user-generated data are associated with an imaginal exposure session conducted within a clinical environment. In certain embodiments, Step 508 comprises one or more steps for launching an instance of the IVE therapy management application on the patient client device (or the clinician client device) and establishing a data transfer interface between the patient client device (or the clinician client device) and one or more physiological sensors. Step 508 may comprise operations for associating the instance of the IVE therapy management application with the imaginal exposure session and configuring a data collection protocol for collecting sensor data from the physiological sensors according to the data collection protocol. Step 510 may comprise operations for launching an instance of the IVE therapy management application on the patient client device and presenting a graphical user interface configured to present one or more data collection workflows and/or form elements and receive one or more user-generated inputs according to the workflows and/or form elements. In accordance with certain embodiments, the workflows and/or form elements may be configured to collect SUDS data from the patient corresponding to the imaginal exposure session. In accordance with certain aspects of the present disclosure, baseline data 522 is communicated to the application server. Baseline data may be communicated to the application server in real-time or in accordance with one or more batch processing protocols. Routine 500 may further comprise one or more operations for receiving baseline data and processing the baseline data to establish one or more baseline values for the patient user profile (Step 512). Routine 500 may comprise one or more operations for configuring an IVE treatment plan for the patient user profile according to the baseline values (Step 514). The baseline values may be incorporated into one or more algorithms for generating one or more treatment plan recommendations and/or for generating one or more treatment plan elements. In accordance with certain embodiments, Step 514 may comprise presenting the baseline data to the clinician client device within an instance of the IVE therapy management application and presenting a graphical user interface comprising one or more workflows for configuring the IVE treatment plan. Routine 500 may further comprise one or more operations for configuring environmental stimuli parameters according to the baseline data (Step 516) and one or more operations for configuring IVE session parameters according to the baseline data (Step 518). The environmental stimuli parameters (Step 516) and the IVE session parameters (Step 518) may be configured by a clinician user within an instance of the IVE therapy management application via the graphical user interface and/or may be configured automatically by the application server via one or more data processing algorithms/application logic. In accordance with certain embodiments, routine 500 may conclude by executing one or more operations for associating the configuration(s) of the IVE treatment plan with the patient user profile and storing the configuration(s) of the IVE therapy plan in the application database (Step 520).

Figure 6:
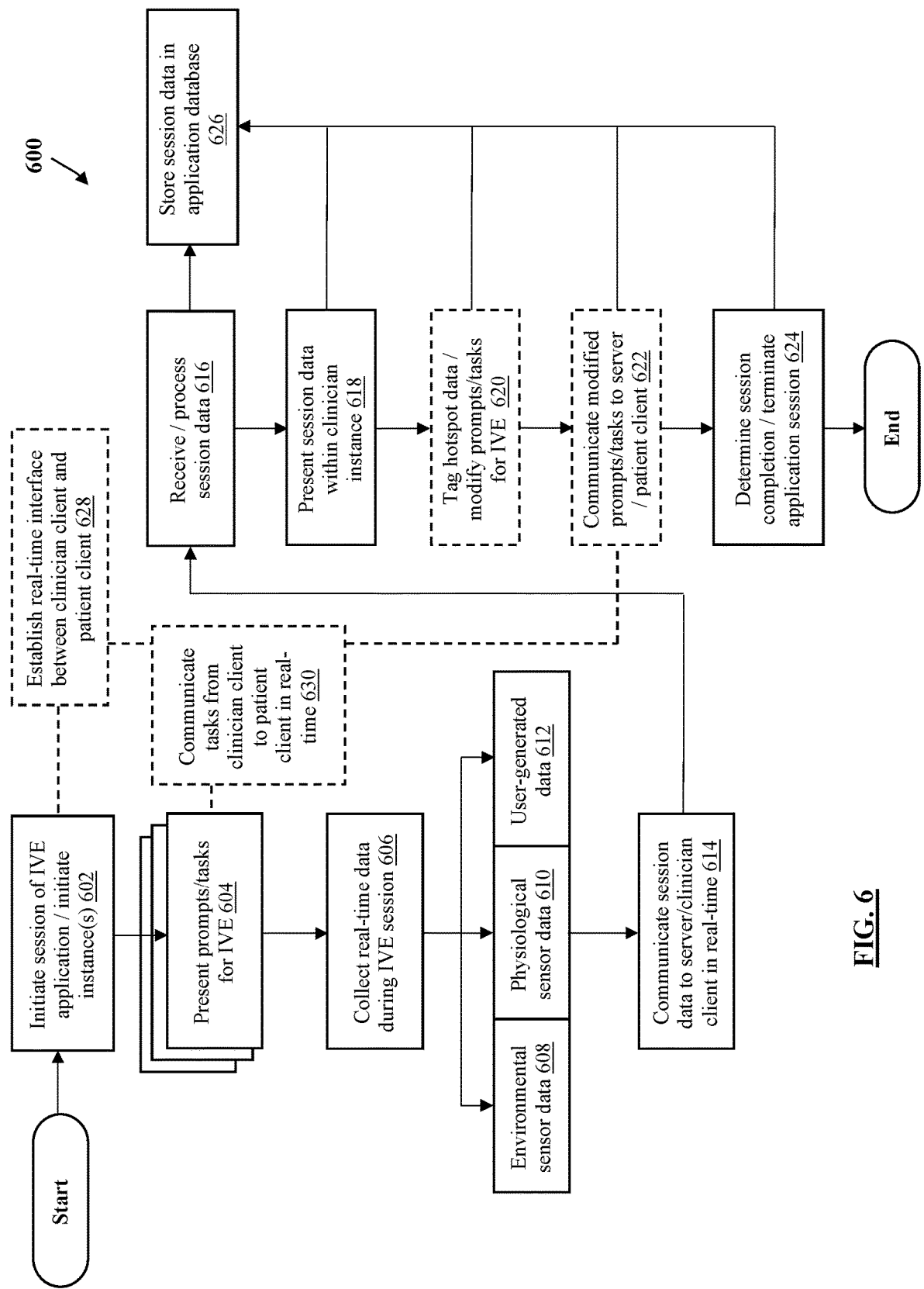
FIG. 6 is a process flow diagram of a routine of a method and system for distributed management of in vivo exposure therapy, in accordance with certain aspects of the present disclosure.

Referring now to FIG. 6, a process flow diagram of a routine 600 of a method and system for distributed management of in vivo exposure therapy is shown. In accordance with certain aspects of the present disclosure, routine 600 may be incorporated within one or more aspects of system 200 of FIG. 2, system 300 of FIG. 3 and/or system 400 of FIG. 4. Routine 600 may be incorporated within one or more process steps of data flow schema 800 of FIG. 8. Routine 600 may be embodied within one or more processor-executable instructions of an IVE therapy management application configured to command one or more operations of a patient client device, a clinician client device and/or an application server, as shown and described in FIGS. 2-4. In accordance with certain aspects of the present disclosure, routine 600 may comprise one or more of process flow steps 602-626. In certain embodiments, one or more of process flow steps 602-626 may comprise one or more sub-steps and/or may be executed via at least one processor of the patient client device, the clinician client device and/or the application server within a networked computing environment. Routine 600 may be executed in sequence with one or more steps of routine 500 (as shown in FIG. 5) and/or may comprise one or more sub-steps of routine 500 (as shown in FIG. 5). Routine 600 may comprise one or more operations for initiating, administering and managing an IVE session within the IVE therapy plan.

Still referring to FIG. 6, routine 600 may be initiated by initiating a session of the IVE therapy management application on the patient client device (Step 602). Step 602 may comprise one or more operations for establishing a real-time data transfer interface between the patient client device and the clinician client device (Step 628). In certain embodiments, the session of the IVE therapy management application may comprise a patient instance, a clinician instance and/or a server instance of the IVE therapy management application. Step 602 may comprise presenting a graphical user interface comprising one or more interface elements for initiating, administering and managing the IVE session for the patient user within the patient instance and the clinician user within the clinician instance. Routine 600 may continue by executing one or more operations for initiating the IVE session on the application server and presenting one or more user prompts and/or tasks for the IVE session to the patient user within the patient instance (Step 604). In certain embodiments, the one or more prompts may be configured from within the clinician instance and/or one or more tasks may be communicated from the clinician client to the patient client in real-time (Step 630). The patient instance may comprise one or more operations for collecting real-time data during the IVE session (Step 606). Routine 600 may comprise one or more data transfer protocols and/or operations for collecting environmental sensor data 608, physiological sensor data 610, and/or user-generated data 612. Step 606 may comprise presenting one or more interface elements within the patient instance configured to prompt the user to provide one or more user-generated inputs comprising the user-generated data 612. Routine 600 may comprise one or more operations and/or protocols for communicating the session data (i.e. environmental sensor data 608, physiological sensor data 610, and/or user-generated data 612) to the application server and/or the clinician client in real-time (Step 614). Routine 600 may comprise one or more operations for receiving and processing the session data at the application server (Step 616) and presenting the session data within the clinician instance of the IVE therapy management application (Step 618). Routine 600 may comprise operations for presenting within the clinician instance one or more interface elements configured to enable the clinician user to perform one or more actions in response to the session data. In accordance with certain embodiments, the one or more actions may comprise identifying one or more "hot spots" within the session data and tagging and/or notating the one or more "hot spots" via the one or more interface elements (Step 620). Step 620 may further comprise one or more actions for modifying one or more patient user prompts and/or tasks for the IVE session via the one or more interface elements. Routine 600 may continue by executing one or more operations and/or protocols for communicating the modified tasks/prompts (if any) to the application server and presenting the modified tasks/prompts via the patient instance executing on the patient client device (Step 622). Routine 600 may continue by executing one or more operations for determining whether one or more session parameters have been satisfied/completed and one or more operations for terminating the session of the IVE application (Step 624). In accordance with certain embodiments, the one or more session parameters may comprise time duration parameters, task completion parameters and/or sensor data threshold parameters. Routine 600 may comprise one or more operations for storing session data within the application database (Step 626). Session data may include all data generated during the session of the IVE application, including activity data from the patient instance, clinician instance and/or server instance of the IVE application session; and/or device data from the patient client device, clinician client device and/or application server. Step 626 may be executed as a background operation of one or more of steps 614-624 within routine 600.

Figure 7:
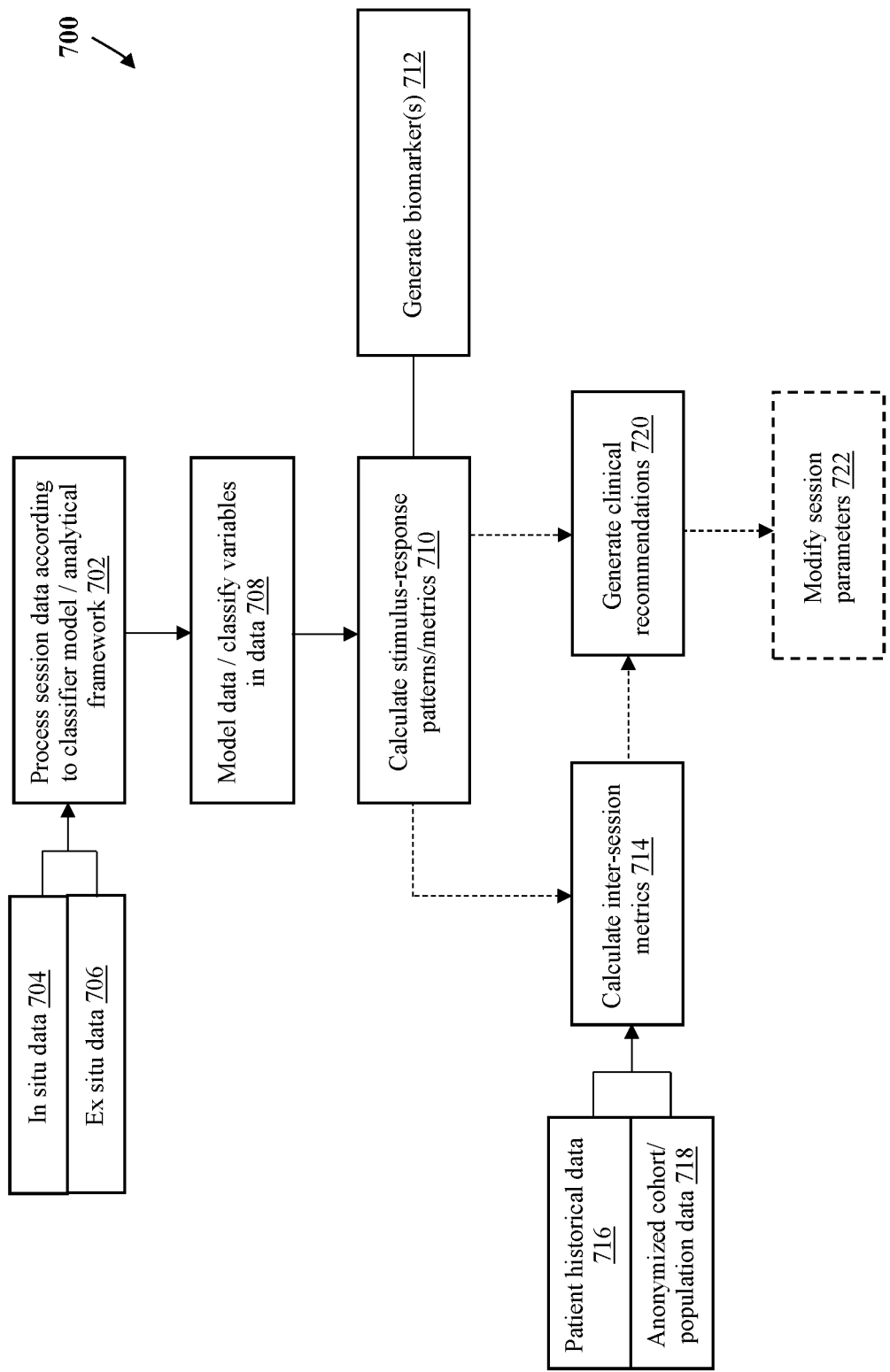
FIG. 7 is a process flow diagram of a routine of a method and system for distributed management of in vivo exposure therapy, in accordance with certain aspects of the present disclosure.

Referring now to FIG. 7, a process flow diagram of a routine 700 of a method and system for distributed management of in vivo exposure therapy is shown. In accordance with certain aspects of the present disclosure, routine 700 may be incorporated within one or more aspects of system 200 of FIG. 2, system 300 of FIG. 3 and/or system 400 of FIG. 4. Routine 700 may be incorporated within one or more process steps of data flow schema 800 of FIG. 8. Routine 700 may be embodied within one or more processor-executable instructions of an IVE therapy management application configured to command one or more operations of a patient client device, a clinician client device and/or an application server, as shown and described in FIGS. 2-4. In accordance with certain aspects of the present disclosure, routine 700 may comprise one or more of process flow steps 702-722. In certain embodiments, one or more of process flow steps 702-722 may comprise one or more sub-steps and/or may be executed via at least one processor of the patient client device, the clinician client device and/or the application server within a networked computing environment. Routine 700 may be executed in sequence with one or more of steps of routine 500 (as shown in FIG. 5) and/or one or more of steps of routine 600 (as shown in FIG. 6). Routine 700 may comprise one or more sub-steps of routine 500 (as shown in FIG. 5) and/or one or more of sub-steps of routine 600 (as shown in FIG. 6). Routine 700 may comprise one or more operations for processing session data, analyzing session data according to one or more analytical frameworks and generating one or more clinical recommendations and/or modifying one or more IVE session parameters within the IVE therapy plan.

Still referring to FIG. 7, routine 700 may be initiated by executing one or more operations for processing session data according to one or more analytical framework and/or classifier model (Step 702). Session data may comprise in situ data 704 (i.e. data collected during an IVE session) and ex situ data 706 (i.e. data collected from outside an IVE session). In situ data 704 and ex situ data 706 may together comprise a raw dataset for processing in accordance with one or more operations of routine 700. Examples of in situ data 704 may include sensor data, user-generated data, and/or device activity data collected from the patient client device and/or the clinician client device during an IVE session. Examples of ex situ data 706 may include sensor data, user-generated data, and/or device activity data collected from the patient client device and/or the clinician client device before or after an IVE session and/or other data sources such as electronic medical record data for the patient or anonymized cohort data. In accordance with certain aspects of the present disclosure, the operations of Step 702 for processing session data according to one or more analytical framework and/or classifier model may include one or more series of operations or sub-operations for modeling the data and/or classifying one or more dependent variables from with the data (Step 708) and/or calculating one or more stimulus-response patterns or metrics from within the data (Step 710) to generate one or more digital biomarkers for the patient (Step 712). The digital biomarkers from Step 712 may comprise the output of the analytical framework and data processing operations of Steps 702, 708 and 710 and may be used as leading indicators to predict one or more patient outcomes and determine one or more clinical recommendations in Step 720.

Step 702 may comprise one or more operations for identifying a primary endpoint and/or dependent variable from within the raw dataset. The primary endpoint or dependent variable may comprise at least one diagnostic variable indicative the severity of the patient's condition or prognostic variable indicative of a patient's likelihood of experiencing symptoms of a psychological disorder in response to certain conditions and/or triggers. Step 702 may comprise one or more operations for applying the primary endpoint or dependent variable to generate one or more linear or non-linear quantitative function, value, score, scale, measure, or the like.

In accordance with certain embodiments, once an independent or dependent function has been determined according to one or more application parameters, one or more model dataset(s) may be created based on the raw dataset. Step 708 may comprise one or more operations for processing the raw dataset to classify one or more variables and/or generate one or more aggregated variables (i.e., raw input data can be rolled up to create new variables or to reduce the size of the input data). Types of data typically subject to aggregation may include time series data, spatial data, and spatial-temporal data. For example, data of daily sleep hours can be rolled up to weekly or monthly sleep hours. In certain embodiments, routine 700 may comprise one or more supervised or unsupervised, linear or non-linear, dimension reduction and/or data aggregation framework. Suitable dimension reduction and data aggregation frameworks for use may include, without limitation, Principal Component Analysis (PCA), Multi-Dimension Scaling (MDS), Locally Linear Embedding (LLE), Independent Component Analysis, and Linear Discriminant Analysis. In certain embodiments, reducing dimensionality of input data may comprise applying a PCA algorithm, resulting in output data that is orthogonal in the vector space. In certain embodiments, reducing dimensionality of input data comprises applying a Manifold Learning method to identify one or more non-linear structure(s) in the data. Manifold Learning methods are particularly useful for identifying high dimensional structures of raw input data from the data itself, without use of predetermined classifications.

In certain embodiments, MDS may be employed for projecting high dimensionality data into a lower dimensional surface. In such embodiments, observations include a similarity distance delta for input into the algorithm. Outcomes are provided as vectors of coordinates for each data point in a x-dimensional with the objective being to find representatives of K for a given input data set. The representatives of K are called "cluster centers" or "centroids," and are selected so as to have a minimum distance from each data point to a centroid in the same.

In still further embodiments, a lower dimension projection of a selected data set is identified or located using LLE, which preserves distances (location) within local neighborhoods. Furthermore, dimensionality of labeled data can be achieved using supervised methods, such as Linear Discriminant Analysis and/or Neighborhood Component Analysis.

In certain embodiments, Step 702, 708 and/or 710 may comprise operations for cleaning the raw dataset before processing of such data by a machine learning model. Common data cleaning techniques may include, without limitation, imputation, capping, and flooring of the data. In accordance with certain aspects of the present disclosure, data cleaning by imputation may incorporate the use of a decision tree. In certain embodiments, one or more leaf node may comprise a class label with a majority of vote training examples reaching the leaf. In a preferred embodiment, each internal node represents a question on at least one feature that will be branching out according to the answers. Each answer generates a set of questions that aid in determining the data and decision-making based on it. The final result of the decision tree indicates the possibility of all scenarios of decision and outcome. In an alternative exemplary embodiment, K-nearest neighbor (KNN) is employed for imputation of missing data. KNN defines a set of nearest neighbors of a sample and substitutes the missing data by calculating the average of non-missing values to its neighbors. Nearest neighbor is measured as the closest values based on the Euclidean distance.

In accordance with certain embodiments, Step 708 may comprise one or more operations for splitting the model dataset for development and validation; applying one or more identified machine learning model(s); and performing model validation. In accordance with embodiments in which a machine learning model is employed, routine 700 may comprise one or more operations for applying a cross-validation (CV) algorithm that requires appropriate data splitting to avoid over-training of the model. Machine learning models suitable for use in embodiments of the present invention may include: deep learning models (e.g., deep Boltzmann machine), deep belief networks, Recurrent Neural Network (RNN), Fully Convolutional Neural Network (FCN), Dilated Residual Network (DRN), Generative Adversarial Network (GAN), and Deep Neural Network (DNN); ensemble, such as random forest, gradient boost machines, boosting, adaboosting, stacked generalization, and gradient boosted regression trees; neural networks, such as perception, back-propagation, Hopfield, ridge regression, LASSO, and elastic; rule systems, such as cubist, one rule, and zero rule; linear regression, such as ordinary least squares regression, stepwise regression, multivariate adaptive regression splines, locally estimated scatterplot smoothing, and logistic regression; Bayesian, such as naïve, averaged one-dependent estimators, Gaussian naïve, and multinomial naïve; decision tree, such as classification and regression, iterative dichotomiser, and condition-decision; instance-based, such k-nearest neighbor, learning vector quantization, and locally weighted learning; and clustering, such as k-means, k-medians, expectation max, and hierarchical.

In accordance with certain embodiments of routine 700, Step 708 may select/apply a data model according to one or more regularized parameter, measured variable, or a particular set of features. Regularization may refer to modification of a learning algorithm in favor of simpler prediction rules to avoid overfitting. In certain embodiments, the processed data from Step 708 is utilized in Step 710 to calculate one or more stimulus-response patterns within in situ data 704 and ex situ data 706. The output of Step 710 may be utilized in Step 712 to generate one or more digital biomarkers for use in future sessions of the IVE therapy management application to improve or enhance treatment and drive patient outcomes.

In accordance with certain embodiments, routine 700 may further comprise operations for applying the output of Step 710 to calculate one or more inter-session metrics for the patient user (Step 714). Step 714 may compare the output of Step 710 to one or more secondary datasets comprising patient historical data 716 and/or anonymized cohort/population data 718 from within the application database. Routine 700 may utilize the output of Step 710 and/or Step 714 to generate one or more clinical recommendations for the clinician user (Step 720). Routine 700 may comprise one or more operations for receiving one or more data inputs from the clinician user in response to the one or more clinical recommendations and modifying one or more session parameters (either in real-time or ad hoc) (Step 722) according to the data inputs from the clinician user.

Figure 8:
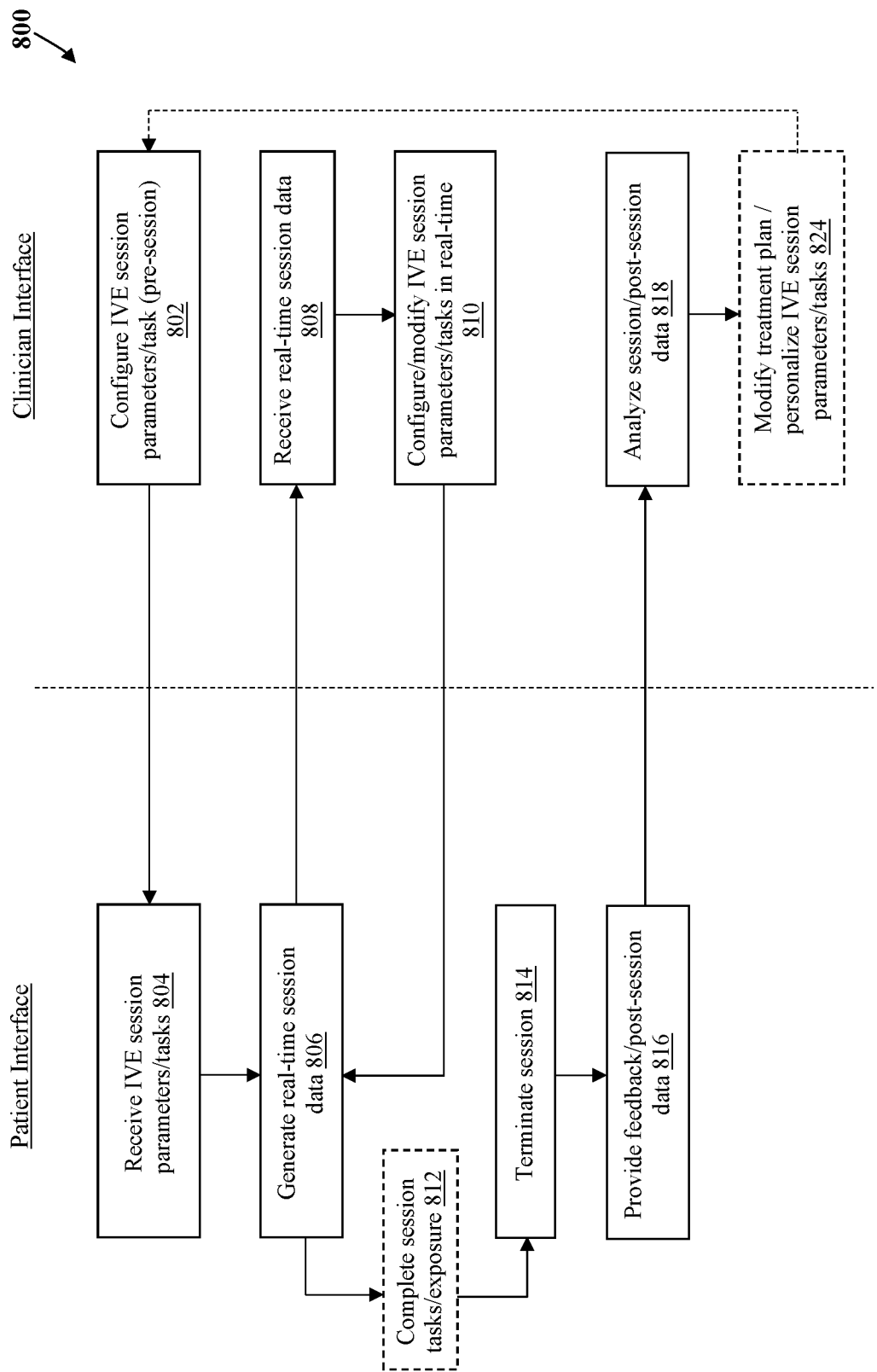
FIG. 8 is a data flow diagram of a method and system for distributed management of in vivo exposure therapy, in accordance with certain aspects of the present disclosure.

Referring now to FIG. 8, a data flow schema 800 of a method and system for distributed management of in vivo exposure therapy is shown. In accordance with certain aspects of the present disclosure, schema 800 may be incorporated within one or more aspects of system 200 of FIG. 2. Schema 800 may be implemented within one or more processor-executable instructions of an in vivo exposure therapy management system, as shown and described in FIGS. 1-4, and/or one or more routines of an in vivo exposure therapy management system, as shown and described in FIGS. 5-7. In accordance with certain aspects of the present disclosure, a clinician user may provide one or more pre-session data inputs within a clinician interface to configure one or more IVE session parameters or tasks 802. The one or more data inputs comprising the one or more IVE session parameters or tasks may be received at a patient interface 804. The one or more IVE session parameters or tasks may be utilized to configure an instance of an IVE therapy management application executing on a mobile electronic device comprising the patient interface. A patient user may launch an instance of the IVE therapy management application within the patient interface and generate real-time session data in response to the one or more IVE session parameters or tasks 806. The real-time session data may be communicated from the patient interface and received at the clinician interface 808. In accordance with certain aspects of the present disclosure, the clinician user may provide one or more data inputs in response to the real-time session data to configure and/or modify the IVE session parameters and/or tasks in real-time. The one or more data inputs comprising the one or more modified IVE session parameters or tasks may be received at a patient interface and drive one or more actions of the patient user to generate real-time session data 806. Upon completion or satisfaction of the one or more IVE session parameters or tasks 812, the IVE session may be terminated at the patient interface 814. Subsequent to terminating the IVE session, the patient user may provide one or more user-generated inputs within the instance of the IVE therapy management application comprising feedback data and post-session data 816. The feedback data and post-session data may be communicated to and received by the clinician interface, and the clinician user may analyze the session data and the post-session data within the instance of the IVE therapy management application executing on the clinician interface 818. The clinician user may provide one or more data inputs within the instance of the IVE therapy management application in response to the session data and/or the post-session data to modify or personalize one or more aspects of the IVE therapy management application, including one or more treatment plan configuration and/or IVE session parameters or tasks 824.

Figure 9:
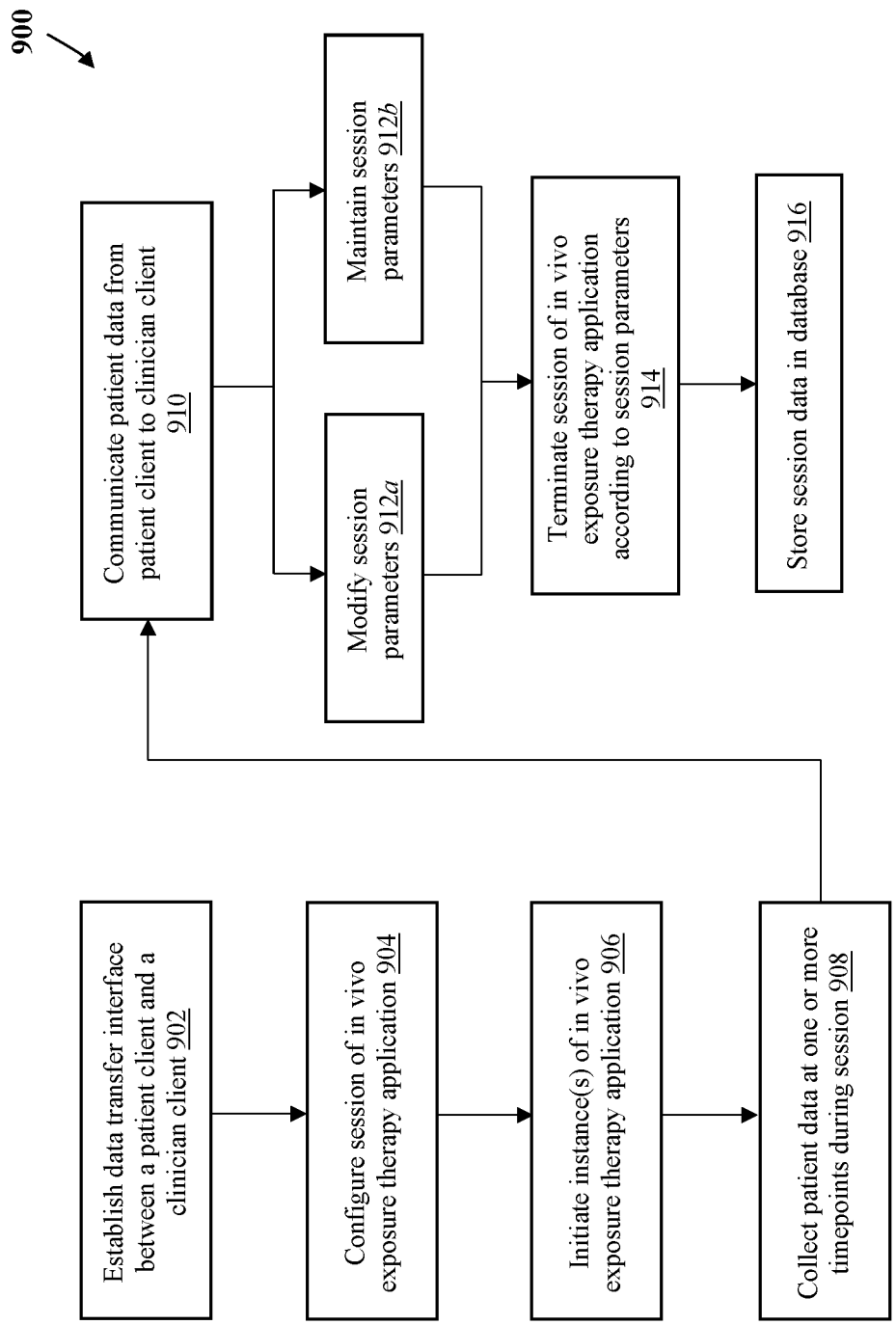
FIG. 9 is a process flow diagram of a method for distributed management of in vivo exposure therapy.

Referring now to FIG. 9, a process flow diagram of a method 900 for distributed management of in vivo exposure therapy is shown. In accordance with various aspects of the present disclosure, method 900 may be incorporated within one or more aspects and/or routines of system 200 of FIG. 2. Method 900 may be implemented within one or more processor-executable instructions of an in vivo exposure therapy management system, as shown and described in FIGS. 1-4 and/or one or more routines of an in vivo exposure therapy management system, as shown and described in FIGS. 5-7. Method 900 may comprise one or more of steps 902-916, which may comprise a process flow for establishing a data transfer interface between a patient client and a clinician client in an in vivo exposure therapy management system, providing an instance of an in vivo exposure therapy management application to a patient user to facilitate an in vivo exposure session, collecting and communicating data from the in vivo exposure session from the patient interface to the clinician interface, and personalizing or improving the in vivo exposure session for the patient user in real-time.

In accordance with certain embodiments, method 900 may be initiated by establishing a data transfer interface between a patient client and a clinician client (Step 902). In accordance with certain embodiments, the patient client and the clinician client may respectively comprise patient client device 204 and clinician client device 222, as shown in FIG. 2. Method 900 may continue by configuring a session of an in vivo exposure therapy management application on an application server (Step 904). Method 900 may continue by initiating an instance of the in vivo exposure therapy application on the patient client and the clinician client (Step 906). In accordance with certain embodiments, the instance of the in vivo exposure therapy management application may comprise presenting one or more prompts to the patient client to instruct a patient user to engage in one or more in vivo exposure tasks. The instance of the in vivo exposure therapy management application may also comprise presenting one or more prompts to the clinician client to configure and/or modify the one or more in vivo exposure tasks. Method 900 may continue by collecting patient data at one or more timepoints during the in vivo exposure therapy session (Step 908). Patient data may comprise environmental data, patient physiological data, and/or patient input data. Patient data may be collected via one or more physiological or environmental sensors communicably engaged with the patient client and/or one or more user-generated inputs collected from the patient user via an input device of the patient client. In certain embodiments, the patient data may be collected in real-time or at designated intervals. Method 900 may continue by communicating the patient data from the patient device to the client device via the data transfer interface (Step 910). In some embodiments, the data transfer interface may comprise an application server as an intermediary (i.e. broker) between the patient client and the clinician client. In some embodiments, the patient data may be communicated to the clinician client in real-time or at batch intervals. Method 900 may continue by modifying one or more session parameters in response to the patient data (Step 912a) and/or maintaining the one or more session parameters in response to the patient data (Step 912b). In accordance with certain embodiments, Step 912a and/or Step 912b may be executed in response to one or more inputs by the clinician user at the clinician interface and/or automatically by the application server according to one or more logic flows. Method 900 may continue by terminating the session of the in vivo exposure therapy management application according to one or more session parameters (Step 914). In accordance with certain embodiments, Step 914 may be executed in response to one or more inputs by the clinician user at the clinician interface and/or automatically by the application server according to one or more logic flows or business rules (e.g. in response to expiration of a timing duration or satisfaction of a condition, such as a sensor data threshold). Method 900 may conclude by storing the session data in the application database (Step 916).

Figure 10:
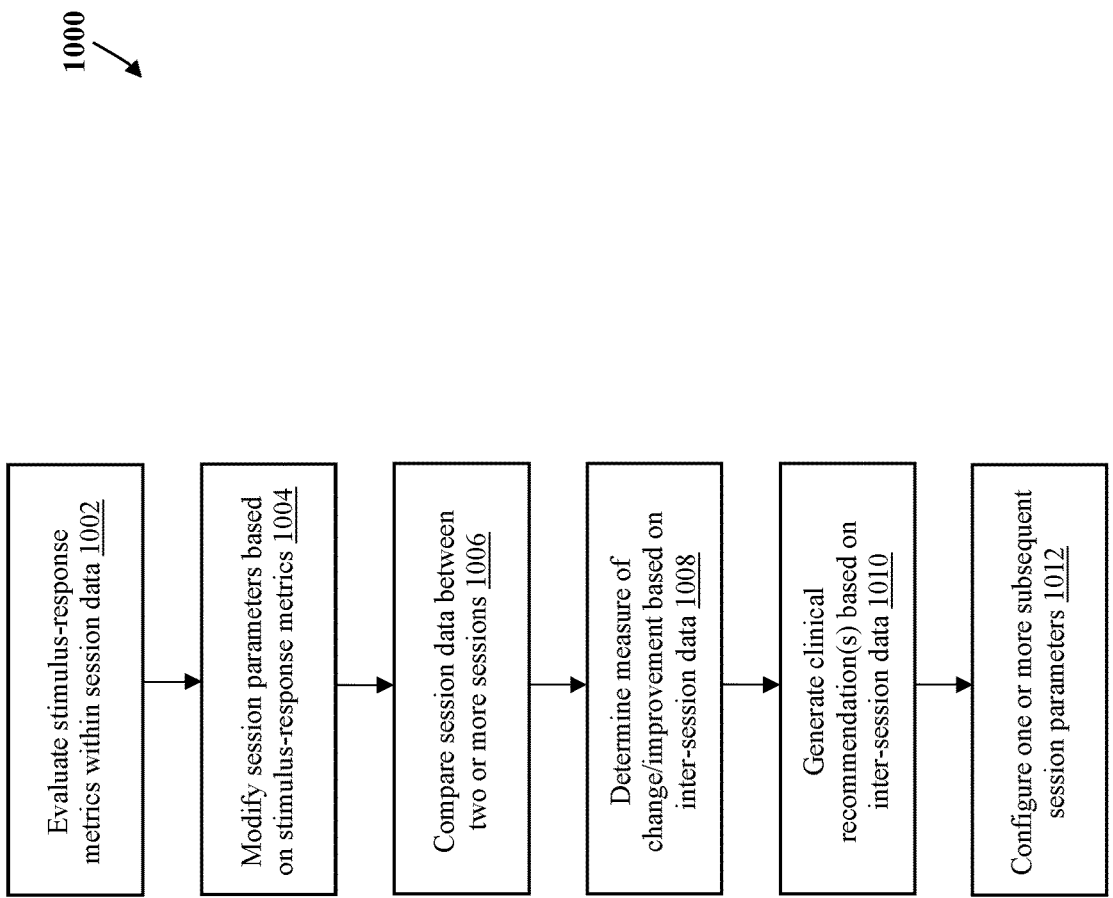
FIG. 10 is a process flow diagram of a method for distributed management of in vivo exposure therapy, in accordance with certain aspects of the present disclosure.

Referring now to FIG. 10, a process flow diagram of a method 1000 for distributed management of in vivo exposure therapy is shown. In accordance with various aspects of the present disclosure, method 1000 may be incorporated within one or more aspects and/or routines of system 200 of FIG. 2. Method 1000 may be implemented within one or more processor-executable instructions of an in vivo exposure therapy management system, as shown and described in FIGS. 1-4 and/or one or more routines of an in vivo exposure therapy management system, as shown and described in FIGS. 5-7. Method 1000 may comprise one or more of steps 1002-1012, which may comprise a process flow for determining one or more quantitative or qualitative treatment metrics for a patient user of the in vivo exposure therapy management system, generating one or more clinical insights for a clinician user of the in vivo exposure therapy management system, and personalizing or improving a treatment plan for the patient user within the in vivo exposure therapy management system. In accordance with various embodiments, steps 1002-1012 may be executed subsequent to, or concurrent with, one or more of steps 902-914 of method 900, as shown in FIG. 9. In certain embodiments, steps 1002-1012 may comprise one or more sub-steps of method 900, as shown in FIG. 9.

In accordance with certain embodiments, method 1000 may be initiated by evaluating one or more stimulus-response metrics within the session data stored in an application database of the in vivo exposure therapy management system (Step 1002). Step 1002 may be executed on an application server of the in vivo exposure therapy management system, optionally in response to one or more inputs from a clinician client device. Step 1002 may comprise processing the session data according to one or more data processing framework(s) or machine learning algorithms, such as those described in FIGS. 5-7 above. Method 900 may continue by modifying one or more session parameters based on the stimulus-response metrics (Step 1004). In accordance with certain embodiments, Step 1004 may be executed in response to one or more inputs by the clinician user at the clinician interface and/or automatically by the application server according to one or more logic flows or business rules. Method 900 may continue by comparing session data between two or more sessions of the in vivo exposure therapy management application for the patient user (Step 1006). Method 1000 may continue by determining a measure of change and/or improvement for the patient user based on comparing the session data between the two or more sessions of the in vivo exposure therapy management application for the patient user (i.e. inter-session data) (Step 1008). In accordance with certain embodiments, Step 1006 and/or Step 1008 may be executed manually by the clinician user by viewing the inter-session data within a graphical user interface of the clinician interface and/or automatically by the application server according to one or more logic flows or business rules. Method 1000 may continue by generating one or more clinical recommendations based on the inter-session data (Step 1010). Step 1010 may be executed by the application server in response to evaluating a measure of change in one or more dependent variables within the inter-session data and associating that change with one or more patient outcomes. In certain embodiments, Step 1010 may further comprise presenting the one or more clinical recommendations at the graphical user interface of the clinician interface. Method 1000 may conclude by configuring one or more subsequent session parameters for the in vivo exposure therapy management application for the patient user in response to the one or more clinical recommendations (Step 1012). In accordance with certain embodiments, Step 1004 may be executed in response to one or more inputs by the clinician user at the clinician interface and/or automatically by the application server according to one or more logic flows or business rules.

Referring now to FIG. 11, a process flow diagram of a method 1100 for distributed management of in vivo exposure therapy is shown. In accordance with various aspects of the present disclosure, method 1100 may be incorporated within one or more aspects and/or routines of system 200 of FIG. 2. Method 1100 may comprise one or more of steps 1102-1112, which may comprise a process flow for evaluating a qualitative or quantitative measure of patient improvement or patient outcomes in response to an in vivo exposure therapy regimen and evaluating treatment efficacy and/or clinician performance for a clinician user of an in vivo exposure therapy management application. In accordance with certain embodiments, steps 1102-1112 may be executed subsequent to, or concurrent with, one or more of steps 902-914 of method 900 (as shown in FIG. 9) and/or one or more of steps 1002-1012 (as shown in FIG. 10). In certain embodiments, steps 1102-1112 may comprise one or more sub-steps of method 900 (as shown in FIG. 9) and/or one or more sub-steps 1002-1012 (as shown in FIG. 10).

In accordance with certain embodiments, method 1100 may be initiated by evaluating patient data across all in vivo exposure sessions within an in vivo exposure therapy plan (Step 1102). Step 1102 may comprise processing inter-session data from the application database and presenting one or more visualizations of the inter-session data at a graphical user interface of the clinician interface. Method 1100 may continue by executing one or more process steps to evaluate a qualitative or quantitative measure of treatment efficacy for the in vivo exposure therapy plan (Step 1104) and evaluate a qualitative or quantitative measure of patient outcomes for the in vivo exposure therapy treatment (Step 1106). Method 1100 may continue by executing one or more process steps to compare the qualitative or quantitative measures of treatment efficacy and patient outcomes for a first patient user with the qualitative or quantitative measures of treatment efficacy and patient outcomes for one or more other patient users within a treatment cohort or across a patient population (Step 1108). In accordance with certain embodiments, Step 1104, Step 1106 and/or Step 1108 may be executed manually by the clinician user in response to viewing the visualization(s) of the inter-session data at the graphical user interface of the clinician interface and/or automatically by the application server according to one or more logic flows or business rules. Method 1100 may continue by executing one or more process steps for evaluating treatment efficacy and/or clinical performance for the clinician user (Step 1110) and generating one or more clinical recommendations to improve treatment efficacy and/or clinical performance for the clinician user (Step 1112). In accordance with certain embodiments, Step 1112 may be executed automatically by the application server according to one or more logic flows or business rules.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions (i.e., computer-executable instructions) may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s). Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrases are used herein, a processor may be "operable to" or "configured to" perform a certain function in a variety of ways, including, for example, by having one or more general-purpose circuits perform the function by executing particular computer-executable program code embodied in computer-readable medium, and/or by having one or more application-specific circuits perform the function.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." As used herein, the terms "right," "left," "top," "bottom,"

"upper," "lower," "inner" and "outer" designate directions in the drawings to which reference is made.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A computer-implemented system for distributed management of in vivo exposure therapy, comprising:
  a patient interface comprising a mobile computing device having at least one input/output interface and at least one physiological sensor and at least one environmental sensor communicably engaged with the mobile computing device, wherein the mobile computing device is configured to present a graphical user interface of an in vivo exposure therapy application to a patient user;
  a clinician interface comprising a computing device having at least one input/output interface, wherein the clinician interface is configured to present a graphical user interface of the in vivo exposure therapy application to a clinician user; and
  a cloud-based server communicably engaged with the patient interface and the clinician interface via a communications network, the cloud-based server comprising at least one processor and at least one non-transitory computer-readable medium having instructions stored thereon that, when executed, cause the at least one processor to execute one or more operations of a server-instance of the in vivo exposure therapy application, the one or more operations comprising:
  initiating a session of the in vivo exposure therapy application, the session comprising a patient-instance executing on the mobile computing device and a clinician-instance executing on the computing device;
  configuring one or more session parameters for the in vivo exposure therapy application, the one or more session parameters comprising parameters for exposure to at least one environmental stimulus for the patient user;
  receiving, at one or more timepoints, a plurality of patient data from the patient interface, the plurality of patient data comprising physiological sensor data, environmental sensor data and subjective unit of distress data for the patient user in response to the exposure to the at least one environmental stimulus;
  processing the plurality of patient data according to at least one machine learning framework to estimate one or more stimulus-response patterns between two or more of the environmental sensor data, the physiological sensor data and the subjective unit of distress data;
  communicating the plurality of patient data and the one or more estimated stimulus-response patterns to the computing device;
  modifying the one or more session parameters in response to one or more inputs from the clinician user;
  terminating the session of the in vivo exposure therapy application according to the one or more session parameters; and
  storing the plurality of patient data from the session in at least one database.

2. The system of claim 1 wherein the one or more operations further comprise establishing a real-time audio-video interface between the patient interface and the clinician interface.

3. The system of claim 1 wherein the at least one physiological sensor is selected from the group consisting of heart rate sensors, electrodermal activity sensors, respiration sensors, temperature sensors, actimetry sensors, accelerometers, EMG sensors, EEG sensors, and VOC sensors.

4. The system of claim 1 wherein the at least one environmental sensor is selected from the group consisting of cameras, acoustic transducers, temperature sensors, GPS sensors, accelerometers, e-compass, gyroscopes, and humidity sensors.

5. The system of claim 1 wherein the one or more operations further comprise processing the plurality of patient data according to the at least one machine learning framework to classify at least one primary endpoint or dependent variable within the patient data, wherein the primary endpoint or dependent variable comprises at least one diagnostic variable or prognostic variable.

6. The system of claim 5 wherein the one or more operations further comprise processing a classified dataset comprising the plurality of patient data according to the at least one machine learning framework to generate at least one clinical recommendation output, the at least one clinical recommendation output comprising at least one recommended modification to the one or more session parameters.

7. The system of claim 6 wherein the one or more operations further comprise modifying the one or more session parameters according to the one or more estimated stimulus-response patterns.

8. The system of claim 1 wherein the one or more operations further comprise comparing the plurality of patient data from the session to a plurality of patient data from one or more prior sessions of the in vivo exposure therapy application stored in the at least one database to determine a measure of change in the plurality of patient data from the session.

9. The system of claim 8 wherein the one or more operations further comprise modifying one or more subsequent session parameters according to the measure of change in the plurality of patient data from the session.

10. A computer-implemented method for distributed management of in vivo exposure therapy, comprising:
establishing, with a cloud-based server via a communications network, a data transfer interface between a patient client device and a clinician client device;
configuring, with the cloud-based server, a session of an in vivo exposure therapy application, the session comprising a patient instance comprising a graphical user interface of the in vivo exposure therapy application executing on the patient client device and a clinician instance comprising a graphical user interface of the in vivo exposure therapy application executing on the clinician client device;
initiating, with the cloud-based server, the session of the in vivo exposure therapy application;
providing, with the patient client device, one or more user prompts to a patient user according to one or more session parameters, the one or more session parameters comprising parameters for exposure to at least one environmental stimulus;
collecting, with the patient client device, a plurality of patient data at one or more timepoints during the session, the plurality of patient data comprising physiological sensor data, environmental sensor data and subjective unit of distress data for the patient user in response to the exposure to the at least one environmental stimulus;
communicating, with the patient client device via the communications network, the plurality of patient data to the cloud-based server;
processing, with the cloud-based server, the plurality of patient data according to at least one machine learning framework to estimate one or more stimulus-response patterns between two or more of the environmental sensor data, the physiological sensor data and the subjective unit of distress data;
communicating, with the cloud-based server via the communications network, the plurality of patient data and the one or more estimated stimulus-response patterns to the clinician device;
modifying or maintaining, with the clinician client device, the one or more session parameters according to the plurality of patient data and the one or more estimated stimulus-response patterns; and
terminating, with the cloud-based server, the session of the in vivo exposure therapy application according to the one or more session parameters,
wherein the one or more session parameters comprise at least one duration parameter, location parameter and targeted stimulus-response parameter for the exposure to the at least one environmental stimulus.

11. The method of claim 10 further comprising establishing, with the cloud-based server, a real-time audio-video interface between the patient client device and the clinician client device.

12. The method of claim 10 wherein the environmental sensor data comprises a sensor input from at least one environmental sensor selected from the group consisting of cameras, acoustic transducers, temperature sensors, GPS sensors, accelerometers, e-compass, gyroscopes, and humidity sensors.

13. The method of claim 11 further comprising processing, with the cloud-based server, the plurality of patient data according to the at least one machine learning framework to classify at least one primary endpoint or dependent variable within the patient data, wherein the primary endpoint or dependent variable comprises at least one diagnostic variable or prognostic variable.

14. The method of claim 13 further comprising processing, with the cloud-based server, a classified dataset comprising the plurality of patient data according to the at least one machine learning framework to generate at least one clinical recommendation output, the at least one clinical recommendation output comprising at least one recommended modification to the one or more session parameters.

15. The method of claim 14 further comprising modifying, with the clinician client device, the one or more session parameters according to the at least one clinical recommendation output.

16. The method of claim 15 further comprising comparing, with the cloud-based server, the plurality of patient data from the session to a plurality of patient data from one or more prior sessions of the in vivo exposure therapy application stored in at least one database to determine a measure of change in the plurality of patient data from the session.

17. The method of claim 16 further comprising configuring, with the cloud-based server, one or more subsequent session parameters according to the measure of change in the plurality of patient data from the session.

18. The method of claim 10 further comprising configuring, with the clinician client device, one or more subsequent session parameters according to the one or more stimulus-response patterns for the plurality of patient data.

19. The method of claim 17 further comprising generating, with the cloud-based server, one or more recommended parameters for exposure to at least one environmental stimulus according to the one or more stimulus-response metrics for the plurality of patient data.

20. A non-transitory computer-readable medium encoded with instructions for commanding one or more processors to perform one or more operations of an in vivo exposure therapy application, the one or more operations comprising:
- initiating a session of the in vivo exposure therapy application, the session comprising a patient-instance executing on a patient client device and a clinician-instance executing on a clinician client device;
- configuring one or more session parameters for the in vivo exposure therapy application, the one or more session parameters comprising parameters for exposure to at least one environmental stimulus for a patient user;
- receiving, at one or more timepoints, a plurality of patient data from the patient client device, the plurality of patient data comprising physiological sensor data, environmental sensor data and subjective unit of distress data for the patient user in response to the exposure to the at least one environmental stimulus;
- processing the plurality of patient data according to at least one machine learning framework to estimate one or more stimulus-response patterns between two or more of the environmental sensor data, the physiological sensor data and the subjective unit of distress data;
- communicating the plurality of patient data and the one or more estimated stimulus-response patterns to the clinician client device;
- modifying the one or more session parameters in response to one or more inputs from a clinician user;
- terminating the session of the in vivo exposure therapy application according to the one or more session parameters; and
- storing the plurality of patient data and session data in at least one database.

* * * * *